(12) United States Patent
Aarestad

(10) Patent No.: US 11,058,570 B2
(45) Date of Patent: Jul. 13, 2021

(54) DEVICE AND METHOD FOR OPENING AN AIRWAY

(71) Applicant: SOMMETRICS, INC., Vista, CA (US)

(72) Inventor: Jerome K. Aarestad, Escondido, CA (US)

(73) Assignee: SOMMETRICS, INC., Vista, CA (US)

( * ) Notice: Subject to any disclaimer, the term of this patent is extended or adjusted under 35 U.S.C. 154(b) by 200 days.

(21) Appl. No.: 16/071,880

(22) PCT Filed: Jan. 20, 2017

(86) PCT No.: PCT/US2017/014397
§ 371 (c)(1),
(2) Date: Jul. 20, 2018

(87) PCT Pub. No.: WO2017/127723
PCT Pub. Date: Jul. 27, 2017

(65) Prior Publication Data
US 2019/0021900 A1    Jan. 24, 2019

Related U.S. Application Data

(60) Provisional application No. 62/281,063, filed on Jan. 20, 2016.

(51) Int. Cl.
*A61F 5/56* (2006.01)
*A61F 5/08* (2006.01)
*A61F 5/37* (2006.01)
*A61M 16/00* (2006.01)
(Continued)

(52) U.S. Cl.
CPC .................. *A61F 5/56* (2013.01); *A61F 5/08* (2013.01); *A61F 5/37* (2013.01); *A61H 9/0057* (2013.01); *A61M 16/0009* (2014.02); *A61M 16/06* (2013.01); *A61H 2201/165* (2013.01);
(Continued)

(58) Field of Classification Search
CPC ........ A61H 9/00; A61H 9/005; A61H 9/0057; A61H 2009/0064; A61H 2201/1609; A61H 2201/165; A61H 2205/026; A61H 2205/04; A61F 5/56; A61F 5/08; A61F 5/37;
(Continued)

(56) References Cited

U.S. PATENT DOCUMENTS 5,343,878 A     9/1994   Scarberry et al.
7,182,082 B2 *  2/2007   Hoffrichter ............ A61F 5/055
                                              128/200.24
(Continued)

OTHER PUBLICATIONS

International Search Report and Written Opinion issued in PCT/US2017/014397 dated Apr. 7, 2017.

*Primary Examiner* — Valerie L Woodward
*Assistant Examiner* — Paige Kathleen Bugg
(74) *Attorney, Agent, or Firm* — Acuity Law Group, PC; Michael A. Whittaker

(57) ABSTRACT

The present invention provides devices and methods for creating and/or maintain patency of the upper airway passage. The device is configured to fit under the chin of a subject at an external location corresponding approximately with the subject's internal soft tissue associated with the neck's anterior triangle. The device includes structural elements designed to optimize comfort, compliance and seal achieved through minimizing the pressure variation along the contact surface of the therapy device.

28 Claims, 22 Drawing Sheets

(51) Int. Cl.
*A61H 9/00* (2006.01)
*A61M 16/06* (2006.01)

(52) U.S. Cl.
CPC .............. *A61H 2201/1609* (2013.01); *A61H 2205/026* (2013.01); *A61H 2205/04* (2013.01)

(58) Field of Classification Search
CPC ............ A61M 16/0009; A61M 1/0088; A61M 16/04; A61M 16/06
See application file for complete search history.

(56) References Cited

U.S. PATENT DOCUMENTS

| | | | |
|---|---|---|---|
| 7,762,263 B2* | 7/2010 | Aarestad | A61F 5/56 128/848 |
| 9,820,881 B2* | 11/2017 | Aarestad | A61F 5/56 |
| 10,092,477 B2* | 10/2018 | Grashow | A61H 7/00 |
| 2005/0119700 A1* | 6/2005 | Klobe | A61H 9/005 606/237 |
| 2005/0166929 A1 | 8/2005 | Jiang | |
| 2008/0163875 A1* | 7/2008 | Aarestad | A61F 5/56 128/848 |
| 2009/0123886 A1 | 5/2009 | Vaska | |
| 2011/0066086 A1* | 3/2011 | Aarestad | H01P 5/222 601/11 |
| 2014/0144450 A1* | 5/2014 | Aarestad | A61M 16/0488 128/845 |
| 2014/0277252 A1 | 9/2014 | Hyde et al. | |
| 2015/0173997 A1* | 6/2015 | Grashow | A61H 7/00 601/6 |
| 2017/0143577 A1* | 5/2017 | Aarestad | A61F 5/56 |
| 2017/0196761 A1* | 7/2017 | Hyde | A61M 16/0051 |
| 2018/0125743 A1* | 5/2018 | Aarestad | A61H 9/0057 |
| 2019/0099285 A1* | 4/2019 | Bachelder | A61H 9/0057 |
| 2019/0125572 A1* | 5/2019 | Aarestad | A61F 5/56 |
| 2020/0163822 A1* | 5/2020 | Aarestad | A61H 7/00 |

* cited by examiner

FIG. 9

| Station No. | Flange Total Width | Inside Width | Outside Width | Flange thickness Inside Root | Flange thickness Outside Root | Flange thickness Inside Edge | Flange thickness Outside Edge |
|---|---|---|---|---|---|---|---|
| \multicolumn{8}{c}{Approximate Flange Element Dimensions} |
| 1 | 28.0 | 11.4 | 15.0 | 4.50 | 3.00 | 0.7 | 0.7 |
| 2 | 27.5 | 10.9 | 15.0 | 4.50 | 3.00 | 0.7 | 0.7 |
| 3 | 27.0 | 10.4 | 15.0 | 4.00 | 3.00 | 0.7 | 0.7 |
| 4 | 26.0 | 9.9 | 14.5 | 3.70 | 2.85 | 0.7 | 0.7 |
| 5 | 25.0 | 9.4 | 14.0 | 3.00 | 2.65 | 0.7 | 0.7 |
| 6 | 23.0 | 9.4 | 12.0 | 2.50 | 2.60 | 0.7 | 0.7 |
| 7 | 21.0 | 8.4 | 11.0 | 2.00 | 2.55 | 0.7 | 0.7 |
| 8 | 19.0 | 7.9 | 9.5 | 1.80 | 2.50 | 0.7 | 0.7 |
| 9 | 17.5 | 7.9 | 8.0 | 1.60 | 2.40 | 0.7 | 0.7 |
| 10 | 17.0 | 8.4 | 7.0 | 1.60 | 2.30 | 0.7 | 0.7 |
| 11 | 17.0 | 8.4 | 7.0 | 1.60 | 2.10 | 0.7 | 0.7 |
| 12 | 17.5 | 7.4 | 8.5 | 1.80 | 1.90 | 0.7 | 0.7 |
| 13 | 19.0 | 7.4 | 10.0 | 1.80 | 1.80 | 0.7 | 0.7 |
| 14 | 20.0 | 6.4 | 12.0 | 1.80 | 1.60 | 0.7 | 0.7 |
| 15 | 21.0 | 6.4 | 13.0 | 1.80 | 1.55 | 0.7 | 0.7 |
| 16 | 22.0 | 6.4 | 14.0 | 1.80 | 1.50 | 0.7 | 0.7 |
| 17 | 23.0 | 6.9 | 14.5 | 1.50 | 1.40 | 0.7 | 0.7 |
| 18 | 24.5 | 7.9 | 15.0 | 1.30 | 1.30 | 0.7 | 0.7 |
| 19 | 26.0 | 9.4 | 15.0 | 1.20 | 1.25 | 0.7 | 0.7 |
| 20 | 28.0 | 11.4 | 15.0 | 1.00 | 1.20 | 0.7 | 0.7 |

DEVICE AND METHOD FOR OPENING AN AIRWAY

CROSS-REFERENCE TO RELATED APPLICATIONS

The present invention is filed under 35 U.S.C. § 371 as the United States national phase of International Application No. PCT/US2017/014397, filed Jan. 20, 2017, which designated the United States and claims priority from U.S. Provisional Application No. 62/281,063, filed Jan. 20, 2016, each of which is hereby incorporated by reference in its entirety, including all tables, figures and claims.

BACKGROUND OF THE INVENTION following discussion of the background of the invention is merely provided to aid the reader in understanding the invention and is not admitted to describe or constitute prior art to the present invention.

The external application of negative pressure to patients for palliative or therapeutic purpose is well established in the medical arts.

U.S. Pat. Nos. 5,343,878, 7,182,082, and 7,762,263 describe various devices which purport to utilize external application of negative pressure upon the external neck surface of patients. A therapeutic appliance is typically provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage. In certain embodiments, these appliances can provide a chamber element (e.g., a hollow space filled with air molecules) lying between the interior surface of the chamber element and the throat. The therapy appliance is operably connected to an air pump which is configured to produce a partial vacuum in this chamber element. Application of a therapeutic level of negative pressure in the chamber element elicits movement of the upper airway and may alleviate conditions such as snoring, sleep apnea, and full or partial airway collapse for example.

In these "negative pressure" therapeutic apparatuses and methods it is difficult to obtain a proper and comfortable fit between the apparatus and the patient to create and maintain the differential negative pressure (relative to atmospheric pressure for example) at the desired location on the patient. This is particularly true as the devices are intended for daily wear for many hours; thus, any points of high pressure from the device's sealing flange element on the user's skin soon become too uncomfortable for continued use. Further, success of these negative pressure therapies is optimized by a device's ability to accommodate (flex, bend, flow, etc.) varying anatomical features (i.e. device compliance). User compliance with therapy is maximized by a good comfortable interface between the device and the user. Finally, the device should also accommodate movement to different sleeping positions without loss of seal.

BRIEF DESCRIPTION OF THE INVENTION

It is an object of the invention to provide a therapy device with sealed chamber element and a flange element adapted to form a conforming sealing surface between a device that is intended to attach and seal to a patient's external tissue, such as a face, a neck, an area surrounding a wound, etc. This therapy device is particularly suited for forming a sealed chamber element that is configured for the administration of negative pressure to a targeted therapy on the external tissue of an individual.

In a first aspect, the invention provides therapy devices configured for the administration of negative pressure upon the external surface of the individual. These therapy devices comprise:

a chamber comprising
  (i) a flange element defining a periphery of the chamber element and adapted to form a sealing surface when mated to the individual, wherein a first surface of the flange element is configured to approximately conform to a continuous contact area on the individual defined by a first location approximately corresponding to a first gonion on one side of the individual's mandibular body, a second location approximately corresponding to the individual's mental protuberance, a third location approximately corresponding to a second gonion on the opposite side of the individual's mandibular body, and a fourth location approximately corresponding to the individual's thyroid cartilage,
  (ii) a chamber element affixed to the flange element such that an airtight junction is provided between the flange element and the chamber element, wherein the chamber element is configured to define a chamber overlying the external surface of the individual bounded by the flange element and to apply a force to the external surface of the individual when a therapeutic level of negative pressure is applied within the chamber element, the force sufficient to maintain patency of the upper airway by drawing the external surface of the individual into the chamber element,
  (iii) one or more first recesses located approximately at a junction formed between the flange element and the chamber element approximately corresponding to the second location, the first recesses providing a first hinge region within the chamber element, and
  (iv) one or more second recesses within the chamber element located approximately at a junction formed between the flange element and the chamber element approximately corresponding to the fourth location, the second recesses providing a second hinge region within the chamber element,
wherein the flange element varies in thickness such that the second location is substantially thicker than the first and third locations and the first and third locations are substantially thicker than the fourth location;
wherein the flange element varies in width such that the fourth location is substantially wider than the first and third locations;
wherein the junction formed between the flange element and the chamber element at the first and third locations are positioned on the flange element such that greater than about 50% but less than about 60% of the width of the flange element is positioned within the interior of the chamber element;
wherein the junction formed between the flange element and the chamber element at the fourth location is positioned on the flange element such that less than about 50% but more than about 40% of the width of the flange element is positioned within the interior of the chamber element;

wherein the first and second hinge regions and the configuration of flange element and the chamber element are configured (i) to reduce the transmission of deformational strain within the chamber element relative to a chamber element lacking the first and second hinge regions and (ii) to reduce non-uniform force loads applied by the flange element when the chamber element is mated to the individual and the therapeutic level of negative pressure is applied within the chamber element by approximately equalizing the sum of hoop stress and truss stress across the continuous contact area; and an air pump operably connected to the chamber element to produce the therapeutic level of negative pressure within the chamber element.

The terms "external area" and "external surface" of an individual as used herein refers to a portion of the external skin surface of the individual. In various embodiments, the therapy device is configured to provide optimized fitting parameters, for example, seal, comfort and local device compliance throughout all points of contact. This is preferably achieved by minimizing the contact pressure differential from one point of contact on the skin of a patient to another through design features of the flange element and design features of the sealed chamber element of a negative pressure therapy device.

Preferably, the one or more first recesses and/or the one or more second recesses are within the chamber element. In certain embodiments, the chamber element comprises two first recesses approximately positioned at the individual's mental tubercles. These two recesses are preferably voids in the material of the chamber element, most preferably in the internal surface of the chamber element. The two recesses are most preferably positioned laterally from one another so as to flank the chin of the wearer.

In certain embodiments, the location on the width dimension of the flange element at which the junction is formed between the flange element and the chamber element varies around the circumferential dimension of the flange element. By varying the junction, the magnitude of forces applied to the skin surface of the individual can be varied from point to point around the continuous contact area. In this manner, the force applied to the external surface of the individual at any point along the circumferential dimension of the flange element may be made to be "constant." In this context, the term "constant" as used herein, refers to maintaining the force within about 20%, and more preferably about 10%, of the average force along the entire circumferential dimension of the flange element, where the force at each point along the circumferential dimension of the flange element is measured at the location on the width dimension of the flange element at which the junction formed between the flange element and the chamber element. Preferably, the junction formed between the flange element and the chamber element at the second and fourth locations are positioned on the flange element such that between about 30% and about 50% of the width of the flange element is positioned within the interior of the chamber element. The exterior dimension is measured from the outside edge of the flange element to the midpoint of the flange element/chamber element junction, and the interior dimension is measured from the inside edge of the flange element to the midpoint of the flange element/chamber element junction.

In certain embodiments, the flange element will contact the chamber element at approximately a normal angle, wherein a normal angle is defined as a geometry where the plane of the flange element is perpendicular to the plane of the chamber element at the junction. In further embodiments, the angle at which the chamber element intersects the flange element at the junction that is formed between the flange element and the chamber element varies around the circumferential dimension of the flange element. By varying the angle at the junction, the flange element can be positioned to better follow facial contours and can vary up to 60 degrees from a normal angle. Angling the flange element on the chamber element may also further assist in the even distribution of the magnitude of forces applied to the skin surface of the individual which can be varied from point to point around the continuous contact area. The outer part of the flange (outbound from the hinge like joint with the chamber element) can be further biased so that the outer part of the flange element makes primary contact during installation and final contact during removal or dislodging events for example making the edge of the flange element exterior to the chamber element the first and or last points of contact of the flange element on the user. This angle bias of the outer part of the flange from the flange having a flat contour on the skin can be up to 45 degrees.

In various embodiments, the chamber element is affixed to the flange element as an integral structure, as a unitary structure, or as discrete structures.

In certain embodiments, the flange element comprises a tacky material inherent in, or positioned on, all or a portion of the contact area. By way of example only, the tacky material can comprise a room-temperature vulcanizing (RTV) silicone. The tacky material may be a single layer, or may be a component of a lamination stack of materials positioned on all or a portion of the contact area.

In certain embodiments, the flange element is increased in thickness at the junction formed between the flange element and the chamber element, relative to thickness at the edges of the flange element. This thickness may be varied at different points on the flange element. By way of example, at the first and third locations the flange element thickness at the junction formed between the flange element and the chamber element may be between about 0.05 inches and about 0.120 inches, and the flange element thickness at the edge is between about 0.005 inches and about 0.025 inches; while at the second location, the flange element thickness at the junction formed between the flange element and the chamber element is between about 0.05 inches and about 0.20 inches, and the flange element thickness at the edges is between about 0.05 inches and about 0.120 inches; and at the fourth location, the flange element thickness at the junction formed between the flange element and the chamber element is between about 0.020 inches and about 0.100 inches, and the flange element thickness at the edges is between about 0.005 inches and about 0.020 inches.

In preferred embodiments, the flange element has curved profile on the top surface thereof and a flattened profile on the bottom surface thereof. This type of profile provides the increased thickness at the junction formed between the flange element and the chamber element, relative to the edges thereof.

Any and all air pump types find use in the present invention, provided that a therapeutic level of vacuum can be achieved by the pump. In certain embodiments, the air pump is connected to the apparatus via a hose or tube. Preferably, the air pump is wearable by the patient and is battery powered, and most preferably the air pump is configured integrally to the apparatus. In certain embodiments, the air pump may be a manual squeeze bulb, or may be electric and comprise a piezoelectric material configured to provide an oscillatory pumping motion. It is most preferred that the oscillatory pumping motion operates at a frequency greater than 500 Hz.

In those embodiments where the air pump is configured integrally to the apparatus, the chamber element can comprise an opening into which the air pump engages, wherein when engaged a periphery of the opening forms an airtight seal with the air pump. A compliant sealing ring may be provided within the opening into which the air pump engages. This compliant sealing ring may be provided integrally with the chamber element, and most preferably as a unitary structure with the chamber element. Alternatively, the compliant sealing ring and the chamber element are discrete structures, where the sealing ring may be in the form of a separate o-ring for example. As an alternative to providing the compliant sealing ring as a component of the chamber element, the compliant sealing ring may be provided as a component of the air pump.

In embodiments where the compliant sealing ring chamber element and pump housing are discreet structures, and wherein the compliant sealing ring is an O-ring type sealing element, the O-ring can be compressed between the sealing surfaces of the pump housing and chamber element to create an air-tight seal. Further, the O-ring type sealing element can be in the form of an O-ring gland design wherein a molded or machined channel or groove is provided on either the surface of the pump housing or the surface of the chamber element and an O-ring fitted in the channel such that when the pump housing and chamber element are fitted an air-tight seal is achieved. As an alternative to providing the O-ring type or O-ring gland designed compliant sealing ring as a component of the chamber element, the compliant sealing ring may be provided as am integrated or discrete component of the air pump.

In further embodiments, a compliant sealing ring, being provided integrally with the chamber element, may consist of raised element within the opening where the raised element may be a lip-type seal, also known as radial shaft seals, for example. Alternatively, the lip-type compliant sealing ring and the chamber element are discrete structures, where the sealing ring may be in the form of a separate lip-type seal for example. As an alternative to providing the compliant sealing ring as a component of the chamber element, the compliant sealing ring may be provided as an integrated or discrete component of the air pump.

In certain embodiments, the chamber element comprises one or more vent elements configured to provide an airflow into the chamber element when the chamber element is mated to the individual and the therapeutic level of negative pressure is applied within the chamber element. This airflow is preferably between about 10 mL/min and about 200 mL/min, and most preferably between about 30 mL/min and about 150 mL/min, and still more preferably between about 75 mL/min and about 125 mL/min. The vent element can comprise an aperture and a filter element within the aperture, wherein the filter element comprises a pore size of about 0.25 μm or less, such as a pore size of about 0.1 μm. The filter element can be configured as a replaceable element. The level of airflow can be maintained as a constant value. Alternatively, the level of airflow can vary. In certain embodiments, the level of airflow tied to the therapeutic level of vacuum; that is, a higher level of vacuum can be accompanied by a higher level of airflow due to the differential in pressure between the atmospheric side of the vent elements and the interior of the chamber element. In certain embodiments the vacuum source may be used in a variable manner to maintain the therapeutic level of vacuum within a specified range rather than a single value, and the level of airflow can vary in concert with the level of vacuum.

It is preferred that the chamber element comprises an unloaded spacing measured between the first and third locations that is narrower than a spacing obtained when the chamber element is mated to the individual and the therapeutic level of negative pressure is applied within the chamber element. This unloaded spacing can impart a preload force to the individual by the chamber element prior to the application of negative pressure.

In related aspects, the present invention relates to methods of applying negative pressure therapy to an individual in need thereof, comprising mating a therapy device as described herein to the individual, and applying a therapeutic level of negative pressure within the chamber element, thereby increasing patency of the airway of the individual. Such methods can be for treatment of sleep apnea; for treatment of snoring; for treatment of full or partial upper airway collapse; for treatment of full or partial upper airway obstruction; for negative pressure treatment of a wound caused by, for example an injury or a surgery; etc.

BRIEF DESCRIPTION OF THE DRAWINGS

FIG. 9 is a table showing approximate flange element dimensions along stations 1-20, including total flange element width, width of the flange element inside the root "inside width", width of the flange element outside the root "outside width", flange element thickness inside and outside the root, and flange element thickness at the inner and outer edges of the flange element.

DETAILED DESCRIPTION OF THE INVENTION

Figure 1:
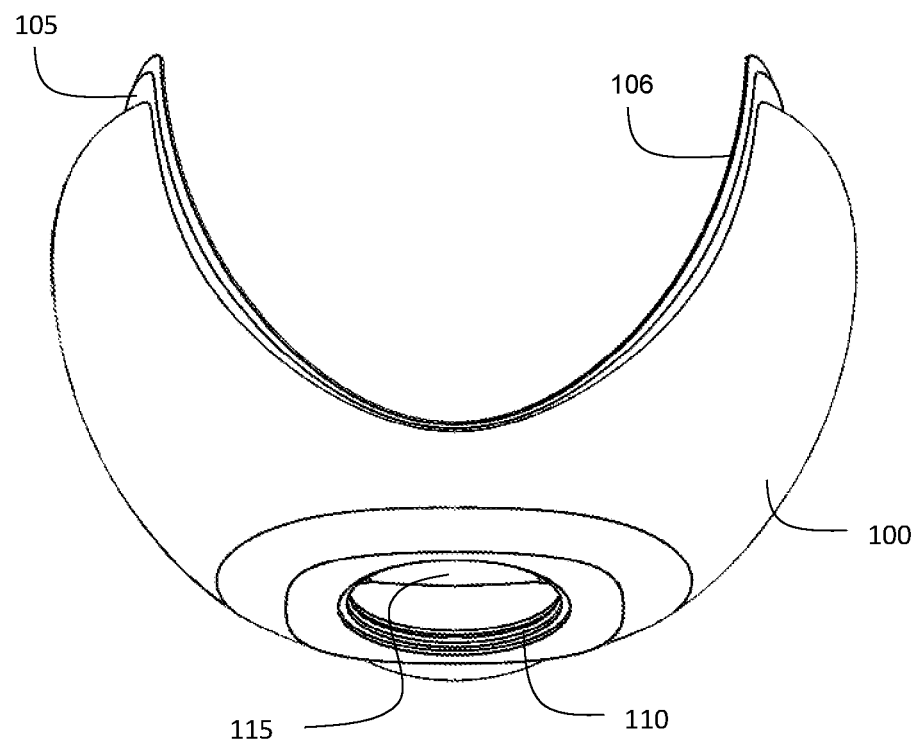
FIG. 1 is top view of an illustrative embodiment of the therapy device including the chamber element 100, flange element 105, flange element/contact surface of the flange element 106, O-ring element 110 and air pump aperture 115.
Figure 2:
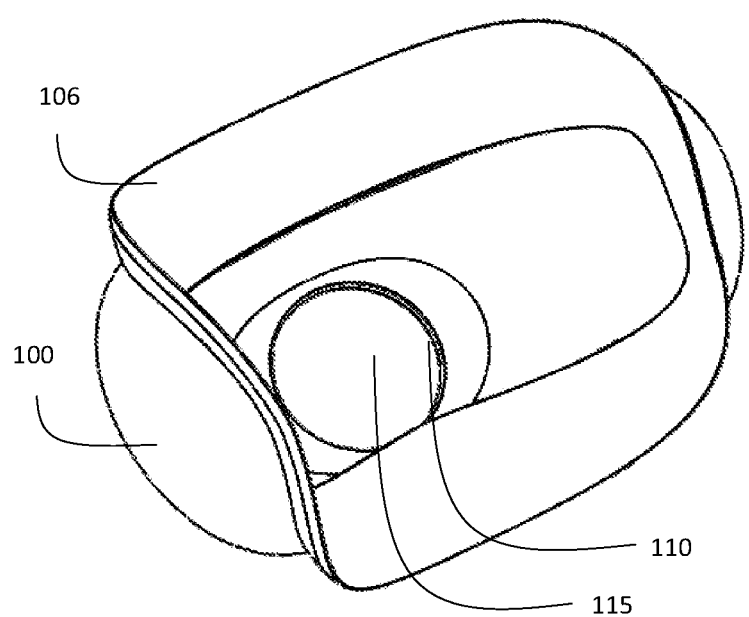
FIG. 2 is a rear view of an illustrative embodiment of the therapy device including the chamber element 100, contact surface of the flange element 106, O-ring element 110 and air pump aperture 115.
Figure 3:
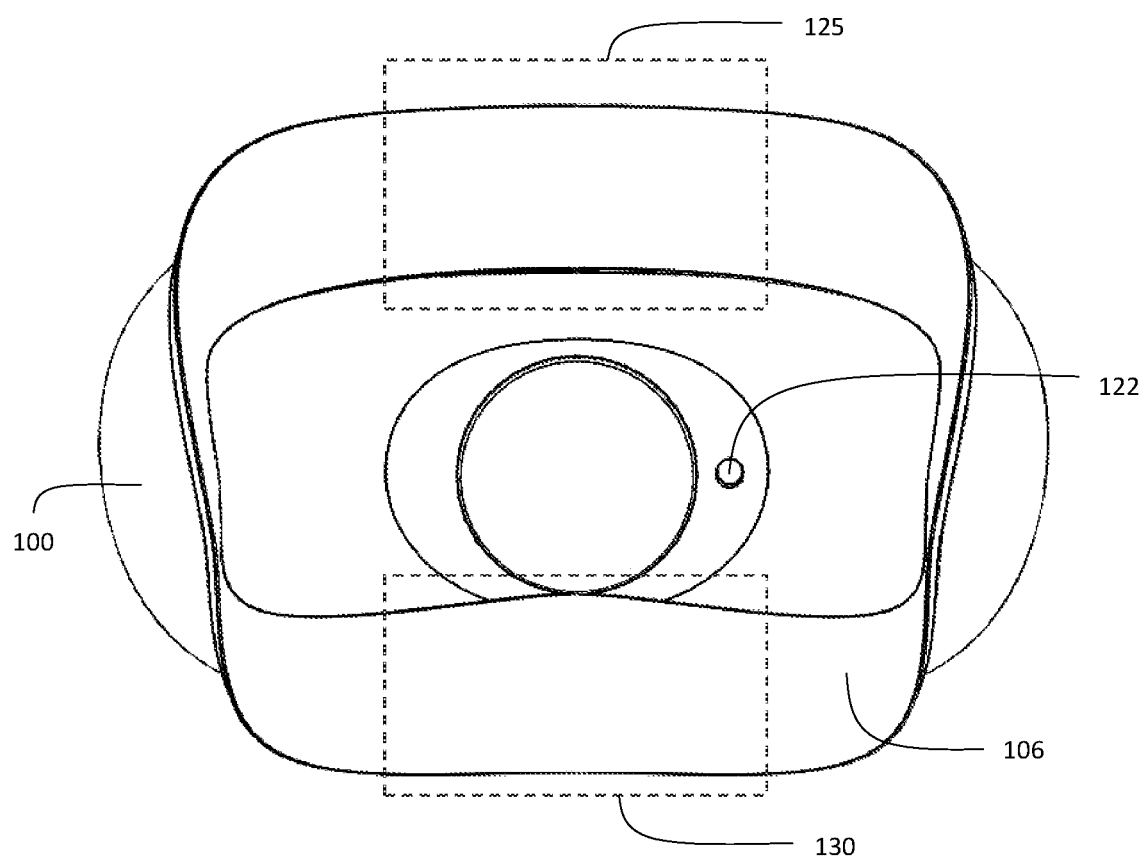
FIG. 3 rear view of an illustrative embodiment of the therapy device including the chamber element 100, the contact surface of the flange element 106, air pump orientation tab 122, upper region(s) of hoop stress 125 and lower region(s) of hoop stress 130, corresponding to features on the individual at the second location, at approximately the chin/mandible and fourth location, at the lower neck at approximately the laryngeal prominence respectively.
Figure 4:
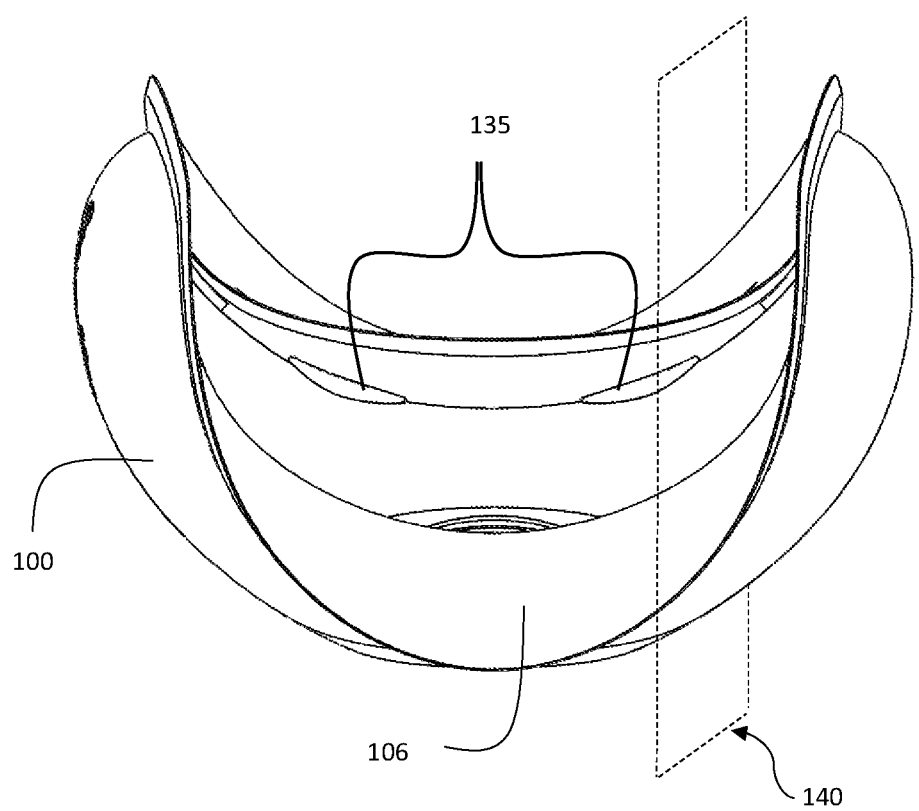
FIG. 4. is a rear view, looking from bottom to top of an illustrative embodiment of the therapy device including the chamber element 100, contact surface of the flange element 106, 135 and a cross-sectional plane 140 for illustration purposes in FIG. 5.

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

In the present invention, a therapy device is designed for a negative pressure therapy device that maximizes comfort and seal efficiency ultimately optimizing device efficacy and user compliance. The negative pressure therapy device is described below for use in the opening of the upper airway when placed upon the neck of a subject over a surface corresponding to approximately the upper airway of the subject. This exemplary application of the technology is not meant to be limiting. The therapy device comprised of a chamber element and a flange element configured to be the contacting surface between the chamber element and the user described herein is configured to provide for regional load equalization over the interface between a negative pressure therapy device and the three dimensionally varying skin surface of the user so as to maintain a near uniform contact pressure over this non-uniform surface.

In particular, the therapy device referred to herein relates but is not limited to an external therapy appliance for relieving upper airway obstruction. U.S. patent application Ser. Nos. 12/002,515, 12/993,311 and 13/881,836 which are hereby incorporated by reference in their entirety including all tables, figures and claims, describes a therapy appliance for relieving airway obstruction. Increasing the patency of the upper airway of an individual alleviates conditions such a snoring, sleep apnea, full or partial upper airway collapse. As described therein, a device is configured to fit under the chin of a user at an external location corresponding to the soft tissues overlying the upper respiratory passages of the neck.

For purposes of the patent application, the term "about" refers to +/−10% of any given value.

The therapy device of the present invention comprises a chamber element and a flange element attached to the edge of the chamber element along the circumferential dimension of the flange element to form an airtight junction between the flange element and the chamber element. The junction between the flange element and the chamber element is referred to herein as the "root" of the junction. The location of this root on the flange element may be varied around the circumferential dimension of the flange element for purposes of contact pressure balancing. An example of this is provided in FIG. 9. Because the root is not a point, for purposes of determining the percentage of the flange element width that is inside the vacuum side of the chamber element and the percentage that is outside, the measurement is taken from the midpoint of the root.

As used herein, the term "circumferential dimension" refers to a continuous location along the width of the flange element, in some cases, for example where the chamber element makes continuous contact with the flange element. As used herein, the "root" is the location at which the chamber element contacts the flange element and is of a width enclosed by the thickness of the chamber element. The chamber element may be affixed to the flange element as an integral structure, unitary structure or discreet structures. An "integral structure" refers to a structure that is a complete piece formed by joining two or more components which, once joined, become a single piece that is not separable without destroying the device. A "unitary structure" refers to a structure that is a singular structure formed or molded as a single piece. Two elements are "discreet structures" if the two (or more) structures form a single working structure, but retain individual characteristics and can be separated in the normal course of use of the single working structure and then reassembled.

Surface variation of the therapy site, both permanent and occasional (i.e., the shape of the mandible, transition points from neck to mandible, tissue types, scars, facial hair and/or skin blemishes differential forces applied to different portions of the seal caused by movement of the wearer, etc.) can undesirably disrupt the seal between the negative pressure therapy device and user. The present invention provides devices, systems and methods of use that can accommodate varying facial contours/features and adapt to movement, resulting in greater comfort, reduced vacuum leakage and improved therapeutic efficacy.

The chamber element and the flange element of the sealing surface incorporate cantilever-like structures, hoop load-like structures and or a combination of the two, adapted to have sectional properties that allow for stiffness, flexibility and uniform regional compliance and/or force load on the skin surface of the individual. As used herein, "regional compliance" refers to a property of the device that permits the device to "mold" itself to a surface and or surface variation on the contact surface with the wearer. As described hereinafter, uniform regional compliance is provided, in part, by the sectional properties or structural features associated with a region on the chamber element, flange element or both.

The flange element preferably comprises a flexible, elastic material that can be uniform in thickness and width but also vary in thickness and width to achieve the structural properties desired at locations along the contact surface of the therapy device. The flange element may further contain a curved profile on the top surface and a flat profile on the bottom surface. The top surface of the flange element being that which makes contact with the chamber element and the bottom surface of the flange element being that which makes contact with the skin of the user. As used herein a "curved profile" describes the shape of a flange element that is thicker at the junction between the flange element and chamber element and thinner towards the outer edges thereof. This is depicted in FIG. 6d for example. In this figure, the axes X and Y indicate the width and thickness dimensions of the flange element as those terms are used herein. The flange element as depicted contain edges that taper outwardly for avoiding skin deformation and cutting associated with hard sharp edges.

Optionally, an adhesive layer is located on the surface of the flange element that makes contact with the user. These elements are configured to maintain an approximate uniform contact pressure with minimized pressure variations along the skin of an individual through all points of contact of the therapy device on a patient. By "minimized pressure variation" means a pressure at any point between the contact surface of the flange element and the patient's tissue varies by no more than about 20%, and preferably no more than about 10% or about 5%, from the average pressure across the entire contact surface. The outer contact surface, as used herein, is the surface of the flange element of the therapy device that makes contact with the skin of the individual forming the contact and sealing surface of the therapy device.

In certain embodiments, the flange element of the invention provides a contact interface of a negative pressure therapy device configured to conform to a continuous contact area on the individual at the external area of the neck approximately corresponding to the anterior triangle of the neck. The term "approximately corresponding to" an anatomical location refers to contacting closely to the actual location, shape or size but perhaps not necessarily completely, accurately or exactly.

Figure 15A:
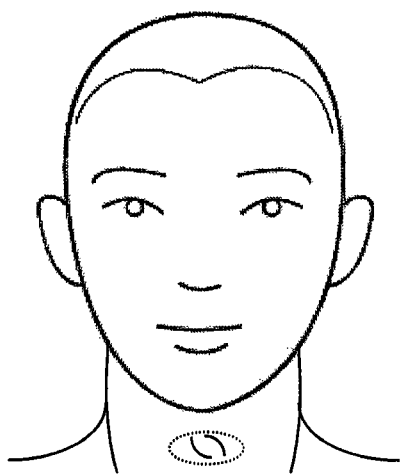
FIG. 15A depicts a region approximately corresponding to the thyroid cartilage bounded by the dotted lines.
Figure 15B:
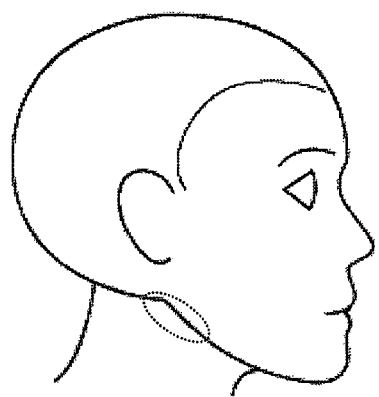
FIG. 15B depicts a region approximately corresponding to gonion bounded by the dotted lines.
Figure 15C:
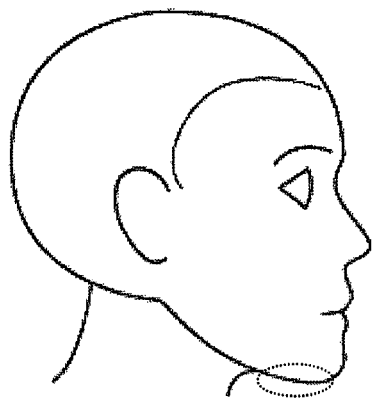
FIG. 15C depicts a region approximately corresponding to the mental protuberance bounded by the dotted lines.

Most preferably, the flange element is configured to follow the contour of the therapy device which is designed to approximately conform to an individual from approximately a first location corresponding to a first gonion on one side of the individuals mandibular body to a second location corresponding to the individuals mental protuberance to a third location corresponding to the second gonion on the opposite side of the individual's mandibular body and a fourth location corresponding to the individuals thyroid cartilage further configured return to approximately the first location corresponding to the first gonion The gonion, as used herein, describes the approximate location on each side of the lower jaw on an individual at the mandibular angle. The mandibular protuberance, as used herein, describes the approximate location of the chin, the center of which may be depressed but raised on either side forming the mental tubercles. The thyroid cartilage, as used herein, describes the approximate location of the large cartilage of the larynx in humans. A region approximately corresponding to the thyroid cartilage is depicted by the dotted lines in FIG. 15A; a region approximately corresponding to the gonion is depicted by the dotted lines in FIG. 15B; and a region approximately corresponding to the mental protuberance is depicted by the dotted lines in FIG. 15C. Note that FIGS. 15B and C show a right profile, and a similar region is present on the left profile.

In certain embodiments, the negative pressure therapy device of the present invention is a chamber element, approximates a dome, oval appearance, with a curvature from the middle of the dome that creates a collar to cover an area over the upper airway of an individual. In preferred embodiments the negative pressure therapy device contains structural elements adapted to guide correct placement and orientation of the device on the user, for example a chin cup element. As used herein a "chin cup" refers to a discreet feature on the negative pressure therapy device which provides a recess configured to receive the chin of the wearer when the negative pressure therapy device is properly mated to the wearer. During application of the negative pressure therapy device, the chin cup provides a consistent point of reference on which the negative pressure therapy device can mate with the wearer. The shape of the chin cup may vary to allow for anatomical variation in patients. For example, the chin cup may be somewhat deeper for use in a subject having mandibular prognathia; somewhat shallower for use in a subject having mandibular retrognathia; or somewhat larger in volume for a subject having macrogenia.

In various embodiments, the present invention comprises a symmetric vacuum chamber element with a flat contact surface adapted to fit to a flat uniform surface and to provide minimized pressure variation throughout all points of contact when a vacuum is applied. In other various embodiments, the present invention comprises a vacuum chamber element with a contact surface configured to adapt to the inherent anatomical variations of an individual's face. The curved, "wraparound" shape that the negative pressure therapy device must assume can cause the "station load" through different contact points to vary in the absence of the design features described herein. For example, absent a feature or features designed to accommodate for station load variation, at points furthest from the center of the dome of the therapy device, toward the narrow end portions of the oval, the station load decreases due to a lesser vacuum cross section over the contact point(s). As used herein, "station load" is the force or pressure which is applied at a discreet area of contact of the device (a "station") on the skin of an individual when the device is mated to the individual and a therapeutic level of negative pressure is applied.

In certain embodiments, the present invention comprises a chamber element having a shape that when unloaded, i.e. not on the patient, spacing between the first and third locations is narrower than the spacing that is obtained when the chamber element is mated to the individual and a therapeutic level of negative pressure is applied. The narrower spacing of the unloaded device creates a preload force that is applied to the individual by the chamber element prior to the application of negative pressure.

As discussed herein, the flange element of the instant invention forms the interface between the chamber element of the therapy device and the contact surface of the individual. The chamber element of the instant invention forms the dome/chamber element of the therapy device. These elements comprise structural features that provide minimized pressure variation at stations where contact pressure variation can occur as a result of either anatomical variation, tissue variation, inherent therapy device design, and or movement during usage. The flange element and chamber element thereby providing features to the therapy device to minimize peak contact pressure values, minimize the variance from station to station and equalize the contact pressure of the therapy device when a therapeutic level of negative pressure is applied to provide an effective seal.

The term "seal" as used in this context is not to necessarily imply that a perfect seal is formed between the therapy device and the contact surface of the individual. Rather, a "seal" is a portion of the device which mates to the wearer and maintains a therapeutic level of vacuum. A certain amount of leakage at the seal may be tolerated so long as the desired negative pressure can be achieved and maintained. Preferred operational vacuum levels are in a range of between 7.6 cm to about 61 cm of water. Preferred forces applied to the user's neck tissues in order to assist in opening the upper airway passages are in a range of about 0.5 kilogram to about 6.68 kilograms. The term "about" and "approximately" as used herein with regard to any value refers to +/−10% of that value.

The dome/chamber element enclosed by the chamber element provides a finite volume which must be evacuated to deliver the desired partial vacuum level. Once generated, the partial vacuum will decay at a rate which is primarily controlled by leakage of air into the chamber element past the seal and or features integrated into the dome to provide airflow. In certain embodiments, the chamber element encloses a volume of between 0.5 and 12 in$^3$. Preferably, the leakage is no more than between 0.005 and 0.5 in$^3$/min, and most preferably between about 0.01 and 0.1 in$^3$/min.

The therapy device may comprise one or more vent elements. As used herein a vent element is an aperture through the therapy device that provides airflow in to the chamber element when the chamber element is mated to the individual and a therapeutic level of negative pressure is applied within the chamber element. The aperture(s) can be in any suitable location on the device however in some embodiments the aperture(s) may be located at the top of the chamber element closer to locations one and three on the individual. The vent element(s) may simply be an aperture such that when the chamber element is mated to the individual and a therapeutic level of negative pressure is applied an airflow between about 10 mL/min and about 60 mL/min is achieved or an aperture through which a filter element can be inserted to create filtered airflow such that when the chamber element is mated to the individual and a therapeutic level of negative pressure is applied an airflow between about 10 mL/min and about 60 mL/min is achieved. The filter element can be a replaceable element and comprise a pore size of between about 0.25 μm and 0.1 μm or less such that when the chamber element is mated to the individual and a therapeutic level of negative pressure is applied an airflow between about 10 mL/min and about 60 mL/min is achieved. In certain embodiments the airflow is between about 30 mL/min and about 50 mL/min.

The present invention provides both sufficient regional, and overall, compliance of the therapy device such that local bottoming/regional collapse of the device does not occur under load. As used herein, "regional compliance" of the device refers to the ability of individual stations of the device to accommodate a therapeutic level of vacuum without complete compression at that station. As used herein, "overall compliance" of the device refers to the ability of the device to accommodate a therapeutic level of vacuum without complete compression of the device. Further, bottoming or "regional collapse", as used herein, is defined as a complete or near complete compression of the device that its resistance to further compression is no longer possible. This results in a hardening of supporting structure(s) by the flexible portions of the device under a heavy load, and loss of comfort by the wearer.

The flange element and chamber element are designed to create uniform contact pressure onto the skin of the user when a therapeutic level of negative pressure is applied. The flange element is preferably a perpendicular width (wide and narrow) and thickness to achieve the desired contact pressure properties. The perpendicular width component is the total width of the flange element, from the tip of the outside edge of the flange element through the root and to the tip of the inside edge of the flange element. The width of flange element may vary along the peripheral axis of the contact area of the flange element (FIG. 8) to accommodate for station load variations due to non-uniform shape of the therapy device that contains a chamber element, that is oval in shape and further contains a central bend to accommodate the mating surface on the neck of the patient corresponding to approximately the upper airway and maintain a constant contact pressure of the negative pressure therapy device.

In various embodiments, locations on the flange element of the device may be substantially wider than other locations. In one aspect the total flange element width may vary from approximately 28.0 millimeters to approximately 17.0 millimeters, (FIG. 9). "Substantially wider" as used herein refers to an increase in width of at least about 10%, more preferably at least about 20%, and still more preferably at least about 30% or more from one location to another, for example in an embodiment of the invention the width of the flange element at the fourth location corresponding to approximately the middle of the neck of the user is approximately 39% wider than the first and third locations that corresponding to the mandible and gonion regions of the user. Wider sections may be found in regions where a larger load displacement is needed for example at the second and fourth locations and narrower sections may be found in regions where smaller load displacement is needed for example at the first and third locations on the user.

The thickness of the flange element may also vary along the perpendicular width along the circumference of contact surface of the therapy device to accommodate for anatomical variation and varying vacuum cross section. As used herein, thick or thin, describes the distance between the surface of the flange element contacting the individual and the (distal) surface of the flange element contacting the chamber element of the vacuum chamber element of a negative pressure therapy device. The thickness of the flange element at the root may vary from approximately 4.5 millimeters to 1.0 millimeters at the inside of the root and 3.0 millimeters to 1.2 millimeters at the outside of the root. For example, the thickness of the flange element at the junction at the first and third locations on the user may be about 1.6 millimeters inside the root and 2.10 millimeters outside the root.

In certain aspects, locations on the flange element of the device may vary in thickness such that some portions are substantially thicker than others. For example, locations of the flange element may vary in thickness such that on location is substantially thicker than another. As used herein, "substantially thicker" refers to an increase in thickness of at least about 20%, more preferably at least about 30%, and still more preferably at least about 50% or more. For example, in an embodiment of the invention the thickness at approximately the second location is approximately 64% thicker that the first and third locations and the first and third locations are approximately 30% thicker than the fourth location.

The thickness of the flange element may further taper outwardly from the root location to a final flange element thickness of approximately 0.7 millimeters to approximately 0.1 millimeters. The taper may begin at the root continuing to the inside or outside edge of the flange element or the taper may also begin at points about 10%, 15%, 20%, 25%, 30%, 35%, 40%, 45%, 50%, 55%, 60%, 65%, 70%, 75%, 80%, 85%, 90% or 95% away from the tip of the flange element and continue to the inside or outside edge of the flange element to a desired final thickness of approximately 0.7-0.1 millimeters. The taper of the flange element at its inner and outer edges assisting in the elimination of edge effects allowing for minimized tissue irritation and damage. As used herein, "edge effects" refer to the irritation, (redness, swelling) of tissue caused by prolonged contact pressure of a sharp edge on the skin. The tapering of edges provides for a more flexible and softer edge of the flange element.

The chamber element is stiff along its length and the flange element will not appreciably deflect longitudinally. Therefore in addressing the dynamic shape of the target therapy area, regions of the therapy device contain accommodating design features, for example, the variations in the width and thickness of the flange element, that are designed to minimize high pressure points and eliminate contact pressure variations of the therapy device along its contact surface when placed on the user and a therapeutic level of negative pressure is applied.

In regions where the flange element contacts a substantially flat surface of the user, the chamber element and flange element can act as an "I-beam" where the force exhibited by the flange element on the user is a more linear downward force and cantilever-like. The flange element inside and outside the root point of the chamber element flex according to the thickness of material with the tapered ends of the flange element flexing the most creating a soft transition on the skin of the user eliminating edge effects as above. As used herein cantilever-like forces are a measurement of the downward force of the chamber element divided by the area of the flange element at a given point. By way of example, in regions where the flange element lays flat across the skin, cantilever forces can be balanced by altering the width and thickness of the flange element, for example where there is a high vacuum cross section and where larger load distribution is desired (ie. lower contact pressure), a flange element with a larger perpendicular width may be utilized and similarly in regions where a smaller load distribution is desired (ie higher contact pressure) a flange element with a smaller perpendicular width may be utilized The thickness dimensions of the flange element can give the flange element properties such that in portions of the device, if the flange element is too thin, though it may be very flexible it will have little to no load distributing properties, can bottom out creating point(s) of high contact pressure from the root of the chamber element resulting in leaks and/or discomfort. If the flange element is too thick it will affect its ability to change direction for example be unable to conform to the acute change from the surface of the neck over the mandible toward the ear for example and further allow for an undesirable level of sheer or lateral movement. In a similar fashion, if the width of the flange element is too small it can create a point(s) of high pressure and too wide it may create unnecessary bulk affecting fit and effective therapy area. Transition in widths taper gradually and the aspect ratio minimizes positional instability and optimizes flexibility.

In regions where the flange element contacts a curved surface of the user, for example around the chin and over the mandible, the forces observed contain an additional hoop-like force component as the flange element bends around those features. "Hoop-like forces" as used herein describe the distribution of force exerted circumferentially, for example, as the flange element travels around location four of the of the user the curvature adds additional stiffness to the flange element inside and outside the root of the chamber element. In these regions where the added force component of hoop loads exists, the thickness of the flange element may be decreased and the perpendicular width of the flange element may be increased to effectively distribute the load of the chamber element and minimize contact pressure variation from station to station when a therapeutic level of negative pressure is applied.

The term "contact pressure" as used herein refers to a pressure imparted on the surface of the skin by the contact surface of the device. It's value can depend on the vacuum present as well as the structural characteristics of the flange element such as the perpendicular width and surface area of the contact surface, and can vary at different locations on the flange element.

A larger "perpendicular width" of a contact surface (meaning the direction that is perpendicular to the longest axis of the contact surface, which longest axis may be curved) will have a lower overall contact pressure under the same vacuum pressure as a contact surface with a smaller perpendicular width due to the increased surface area at that particular station of the contact surface. Therefore, in regions where the dome station pressure load is low, the contact surface of the flange element can be designed to be of a smaller perpendicular width to effectively increase and "balance" the contact pressure and in regions where the dome station pressure is high, the contact surface of the flange element can be designed to be of a larger perpendicular width to effectively decrease and balance the contact pressure where the dome station load is high.

In certain embodiments, the angle of the flange element on the chamber element at the root location could be fixed at a predetermined angle, wherein the angle is fixed around the entire circumferential dimension of the flange element, for example where the flange element is substantially normal (however this angle can vary +/−60 degrees from normal around the periphery of the chamber element to better match local facial contours). The outer edge of the flange can be further biased so that this edge or part of the flange element makes first and or last contact on the user during application, removal and usage of the therapy device. For example, when the flange element is angled such that the outer edge of the flange element exterior to the chamber element is biased inward toward the user's skin, the outer edge of the flange element will become the initial point of contact of the flange element during application of the therapy device. Similarly, when the flange element is angled such that the edge of the flange element interior to the chamber element is angled inward toward the interior of the chamber element, the outer edge of the flange element will become the final point of contact of the flange element during removal of the therapy device. Removal of the therapy device can include taking the device off the user when therapy is complete or include events where the device begins to dislodge during use. With the flange element angled inward toward the chamber element, the edge of the flange element exterior to the chamber element is biased to maintain the seal at the outer edge as long as possible and or until the dislodging event terminates. Angling the flange element on the chamber element may also further assist in the even distribution of the magnitude of forces applied to the skin surface of the individual can be varied from point to point around the continuous contact area.

In certain embodiments the location of the chamber element on the flange element (the root location) may vary from the mid-point, inward or outward to further aid in equalizing the contact pressure of the therapy device on the user when a therapeutic level of negative pressure is applied creating and maintaining the balance point of the flange element on the user. For example, movement of the root of the edge of chamber element on the flange element outward from the mid-point of the flange element effectively increases the vacuum cross section and therefore effective contact pressure of the therapy device at that point when a therapeutic level of negative pressure is applied. Movement of the edge of the chamber element inward has an opposing effect, providing a larger portion of the flange element exposed outside the root location and therapy area decreasing the vacuum cross section. In embodiments of the invention the root location of the chamber element on the flange element is approximately demonstrated in the table in FIG. 9. In regions where higher contact pressure is needed, for example where the device approaches the ear of the user, the chamber element location can be biased on the flange element toward the outer edge increasing the vacuum cross section and effective contact pressure at that point.

In certain embodiments the chamber element may contain features that further aid in the prevent regional collapse, bottoming and transfer of force from one region to another of the therapy device. Absent local points of flexibility, a rigid chamber element may experience situations where external pressure could cause a point of high contact pressure for example upon application of a force, by rolling on to a pillow etc., on the device causing a bottoming event or further a rigid chamber element may experience situations where external pressure on the device on one side causes a transfer of force to the opposite side of the device. Events such as these may cause discomfort, dislodging of the device or both.

In one aspect, the chamber element is formed with one or more recesses positioned therein. In preferred embodiments, the chamber element may contain several recesses. As used herein, a recess refers to a space created by molding a portion of the chamber element thinner than the surrounding material such that when a force is applied the thinner material is able to bend, flex or compress and rebound. The recess is preferably of a thickness to provide the desired properties without rupturing or causing collapse of the chamber element when a therapeutic level of negative pressure is applied.

In certain embodiments one or more recesses are located at points in the chamber element of the therapy device where additional flexibility of the device is needed to reduce point loads where the flange element contacts the user, for example at regions where the device needs to follow anatomical features that rapidly change direction or are particularly hard. By way of example the chin feature, mental tubercles and or the lower neck feature at or around the laryngeal prominence, nearest the second and fourth locations on the user respectively, represent such features. The recess can be of any appropriate shape however in some embodiments the compressible recess is approximately crescent in shape. As used herein a "crescent shape" is described as generally the shape produced when a circular disc has a segment of approximately another circular disc removed from its edge so that what remains is a shape enclosed by two circular arcs of different diameters which intersect at two points. This feature provides a region of compressibility that tapers from regions where larger compression is needed (the middle of the crescent) to regions where less compression is needed (the outer points of the crescent)

In certain embodiments the therapy device may contain one or more first recesses located at approximately at a junction formed between the flange element and the chamber element at approximately the flanks of the chin feature of the chamber element near the mental tubercles of the user, closer to a point nearer to the second location of the user than any of the other locations providing for a first hinge region. Located approximately at a junction, as used herein describes a location closer to one point verses another nearer to where but perhaps not exactly, for example, "one or more first recesses located approximately at a junction formed between the flange element and the chamber element corresponding to the second location" indicates the location of the recess being near a point where the chamber element meets the flange element however not exactly at said junction. As used herein the "flank of the chin" describe the points of the chin where it bends from the front of the face of the user and progresses backwards along the mandible toward the gonion. The bend, creating an anatomical feature where a compressible recess may be beneficial. As used herein the first hinge region is defined as point on the therapy device that can pivot creating a decoupling of one side of the device from the other side of the device.

In certain aspects a recess may be of approximately 0.75 inches in length from tip to tip of the crescent and approximately 0.125 inches in width at the center of the crescent. Further as the compressible recesses flank the chin feature of the device, the compressible recesses may begin at a location approximately 0.5635 inches from the vertical center of the device and progress following approximately the shape and contour of the edge of the chamber element and contact surface of the flange element.

In certain embodiments the therapy device may contain one or more second compressible recesses within the chamber element approximately positioned at a junction formed between the flange element and the chamber element at approximately the lower neck portion of the chamber element nearest the fourth location of the user providing for a second hinge region within the chamber element. The compressible recess may be of a crescent shape that approximately follows the edge of the chamber element and radius/contour of the contact surface of the flange element. The compressible recess may be of approximately 1 inch in length from tip to tip of the crescent and approximately 0.25 inches in width at the center of the crescent.

In certain embodiments the first and second compressible recesses provide for first and second hinge regions that are configured to reduce the transmission of deformational strain within the chamber element relative to a chamber element lacking the first and second hinge regions. A hinge region, as used herein describes a region of the device where one side can bend or pivot independent of the opposite side. The term "deformational strain" as used herein refers to a force applied on the therapy device that causes collapse of the chamber element or disengagement of the device from the individual during use. By way of example, if a user rolls onto a pillow on one side of the device, deformational strain may be transmitted to the other side, causing the device to lift off of the face. The hinge region(s) alone or in combination with other design features described herein effectively allows for a decoupling of force from one side of the device and maintains the device's position on the user and therapy.

The term "balance" as used herein refers to the contact pressure of the therapy device being approximately equal at each station of the contact surface. This contact pressure is proportional to therapy vacuum levels relative to the contact area of the therapy device. For example, in a comparison, a larger contact area vis. a smaller contact area, under the same therapy vacuum level will provide for lower contact pressure of the therapy device respectively. In an embodiment of the invention the contact area of the flange element relative to the therapy area provides for a contact pressure that may range from approximately 0.9 to approximately 1.5 times the vacuum level and in a preferred embodiment the contact pressure of the flange element is approximately 1.2 times greater than therapy vacuum levels.

The chamber element is operably connected to an air pump to produce the therapeutic level of negative pressure within the chamber element. The air pump can be of any type to suitable to produce the therapeutic level of negative pressure for example positive displacement pumps, impulse pumps, velocity pumps, etc. which can include manual squeeze bulbs, rotary pumps, lobe pumps, oscillatory pumps etc. In certain embodiments the air pump comprises a piezoelectric material configured to provide an oscillatory pumping action wherein the oscillatory pumping motion operates at a frequency greater that 500 Hz.

The air pump may be a separate component connected to the chamber element via a hose or tube, or may be configured integrally to the chamber element. The air pump can be connected to the chamber element in any suitable fashion for example an air pump may external the chamber element and connected via a hose or tube, stationary, for example bedside, or battery powered and wearable by the patient. In certain wearable aspects, the air pump is configured to be integral to the chamber element. For example, the air pump may be configured to insert into a sealable aperture on the chamber element, the air pump tightly fitting through the aperture creating a seal. As used herein a sealable aperture is an opening through an element of the apparatus that can be closed or sealed from one side or the other with another element of the apparatus creating an air-tight or water tight seal.

In a preferred embodiment, a seal is created via surfaces designed to receive an O-ring. As used herein an O-ring is a gasket in the form of a compliant sealing ring made of a pliable material designed to be compressed during assembly creating a seal at the interface. In certain aspects a complaint sealing ring feature may be an integral, unitary or discrete part of the air pump, the vessel element or both. In certain embodiments, the compliant sealing ring is provided as a component of the air pump. In a preferred embodiment, the compliant sealing ring feature is a molded feature on the inner circumference of the aperture of the vessel element.

In further embodiments a seal is created via surfaces designed to receive an O-ring gland design where a molded or machined groove or channel is provided on either the surface of the pump housing or the surface of the chamber element and an O-ring is fitted in the groove such that when the pump housing and chamber element are fitted an air-tight seal is achieved. The groove, providing a controlled space, is designed to receive the O-ring where the height of the grooved space is slightly smaller than the O-ring section area such that the O-ring protrudes above the groove. The grooved space can be square or rounded at the base and have a volume larger than the O-ring allowing for the compliant ring to compress freely during assembly. Further the sides of the grooved space can be vertical or angle outward where the base of the groove is narrower than the top of the groove assisting with providing additional volume of the groove.

The O-ring type or O-ring gland design compliant sealing ring can be an integrated or discrete component of the chamber element or may be provided as an integrated or discreet component of the air pump. In embodiments utilizing O-ring gland designs, the insertion of the pump housing into the chamber element causes the protruding surface of the O-ring to make contact with a sealing surface, compressing the O-ring in to the additional volume of the groove and creating an air-tight seal. The effectiveness of the seal can be modulated through the use of compliant sealing rings of varying durometers (range 20 to 70, preferably around 30), height of the compliant sealing ring, depth and width of the groove, inner and outer diameters of the pump housing and chamber element and a combination of two or more of these parameters to give an o-ring gland radial squeeze of 2 to 10% in use.

In further embodiments, a compliant sealing ring is created via surfaces designed to provide and receive a lip seal. As used herein a lip-type seal consists of a substantially cylindrical compliant flange or tang designed to receive and seal statically against a matching substantially cylindrical surface, for example wherein the lip seal is integrated in to the chamber element and the housing of the air pump forms an air-tight seal when inserted into the chamber element. As used herein, substantially cylindrical refers to a shape that includes but is not limited to a round cylinder an oval cylinder and shapes that lack sharp edges wherein a sharp edge can be defined as a point where two vectors intersect creating a corner-like element.

In some examples, a point of contact is formed by two angles, with the vacuum side larger than the exterior side angle. The two angles can be varied to establish differing pressure distribution at the seal contact point. Pressure distribution of the lip-seal can also be varied through the usage of materials of varying hardness (range 20 to 50 durometer), varying thickness (0.6 to 1.2 mm) and varying heights (1 to 3 mm) of the lip seal. The harder, thicker and taller the lip seal, the higher the pressure on the sealing surface. It is desirable to have a seal that is easily created and released by a user while maintaining an air tight seal between the chamber element and pump housing. Further it is desirable to have a flexible seal that allows movement of the pump housing within the chamber element while maintaining the seal. Therefore in a preferred embodiment the lip seal is approximately 0.8 millimeters in thickness, approximately 2.0 millimeters in length, allowing for approximately 1.5 millimeters of movement of the sealing surface using a silicone with a Shore A durometer of approximately 40 when the device is placed on a user and an approximate therapeutic level of negative pressure is applied within the chamber element.

In preferred embodiments the lip-seal is molded in a neutral orientation on the pump aperture of the chamber element such that the lip is not biased inward or outward of the chamber element. Insertion of the pump housing into the chamber element will cause the tip of the lip seal to make contact with the pump housing. As the pump housing is fully inserted the sealing surface between the pump housing element and lip seal will increase along the lip seal as the lip-seal bends inward approximately 90 degrees and lays on the pump hosing element thus creating the air tight seal. In certain examples, the chamber element may be designed with a cavity to receive the lip-seal as it bends in during assembly, including insertion of the pump housing element into the chamber element. The lip-seal feature substantially isolates the sealing feature of the chamber element from the induced structural loads caused by the chamber element during use. As used herein, structural loads of the chamber element can include vertical, horizontal, diagonal, compression of the chamber element for example or any combination thereof.

In preferred embodiments, when the pump housing element is installed in the chamber element, the sealing surface of the lip-seal extends from the tip of the lip-seal, outward toward the exterior air-side of the chamber element to the point where the lip-seal bends and contact is interrupted from the pump housing element. The sealing surface is designed to an appropriate length to accommodate compression and movement of the chamber element such that if the pump housing were to move outward, reducing the sealing surface or the chamber were to experience excessive moment or compression causing a portion of the seal to lift away from the pump housing and the sealing surface is reduced, an air-tight seal would still be maintained when a therapeutic level of negative pressure is applied during use. As used herein an appropriate length is defined as a sealing surface containing a lip seal that is approximately 0.8 millimeters in thickness, approximately 2.0 millimeters in length, allowing for approximately 1.5 millimeters of movement of the sealing surface using a silicone with a Shore A durometer of approximately 40 and able to maintain an approximate therapeutic level of negative pressure when the device is placed on a user and vacuum is applied within the chamber element.

In certain embodiments, some lip seals may contain additional auxiliary lips or ridges along the sealing surface that may serve to protect the primary sealing lip from excessive wear, for example, from contaminants and repeated installation and removal. The lip-seal may also vary in thickness, width, length, material and hardness allowing for control of the rigidity of the lip seal, length of the sealing surface and tightness of the fit between the interfacing surfaces that vary in response to varying levels of negative pressure. In certain aspects of the invention, one or more tangs, tabs and or recesses are present on the chamber element, flange element and or air pump element of the therapy device, which provide one or more guidance feature(s) to ensure a proper orientation of, or mating between one or more device elements. The tangs, tabs and or recesses can be utilized as part of a sensor system to determine various parameters related to use of the therapy device. These parameters can include, but are not limited to, compatibility of the particular air pump element with the therapy device element (e.g., acting as a recognition feature) and correct placement of the air pump element into the aperture of the chamber element. For example, one or more of these tangs, tabs or recesses can be located on the chamber element as a guidance feature for the air pump element such that a recess on the air pump element or chamber element accepts the tang or tab element on the chamber element or air pump element only when the air pump element is inserted through the sealable aperture in the correct orientation. This list is not meant to be limiting.

In certain embodiments, together or with one or more of the foregoing, a material, which will act as an adhesive layer between the flange element of the therapy device and the user, is applied to the outer contact surface of the flange element. The purpose of the adhesive layer is to provide a sealing, cushioning and or sheer absorbing element to the flange element. As used herein sheer refers to sheer strain which is a deformation of a material in which parallel surfaces can slide past one another, for example the contact surface of the flange element and the skin of the user.

The adhesive layer further must preferentially adhere to the outer contact surface of the negative pressure therapy device and provide a sufficient level of "tack" such that a releasable mechanical anchoring of the therapy device to the skin of the user is achieved. Tack, as used herein, refers to a material property at the interface created between the adhesive layer and the device, and the skin of the user at the other interface created between the user and the device.

The adhesive layer may be applied to the contact surface area of the negative pressure therapy device in any suitable method including but not limited to spraying, painting, placing, etc., in single or multiple layers to achieve the desired cushioning and sealing properties including but not limited to thickness, hardness and tack for example. In additional embodiments the adhesive layer may be single layer of a uniform thickness or a single layer of a non-uniform thickness covering the contact surface of the negative pressure therapy device. In further embodiments the adhesive layer may contain a series of parallel adhesive beads spanning the circumference of the contact surface of the negative pressure therapy device wherein the beads can be of a uniform or non-uniform thickness and of a like or varying adhesive and or gel-like material to achieve the desired cushioning and sealing properties.

In certain embodiments the adhesive layer is present on the contact surface of the negative pressure therapy device at a thickness falling within a range of approximately 0.005-0.060 inches. In certain embodiments the adhesive layer is present on the contact surface of the negative pressure therapy device at a thickness falling within a range of approximately 0.010-0.050 inches. In further embodiments the adhesive layer is present on the contact surface of the negative pressure therapy device at a thickness falling within a range of approximately 0.020-0.040 inches.

The adhesive layer may be achieved by using various materials, such as, but not limited to gel, elastomer, viscous solutions, foams and materials of the like. These materials can be of any chemical composition which provides the necessary end use properties (i.e. tack, firmness, medical clearance, etc.). These materials include, but are not limited to polyurethanes, silicones, acroylnitrile butadiene styrene (ABS), hydrogels, and the like. In preferred embodiments, the adhesive layer should have a hardness as measured by ASTM-D2240-00 (American Society for Testing Materials) of between 0 and 50, more preferable between 5 and 30 most preferable between 5 and 15. In certain embodiments the adhesive layer is made of a silicone gel material. The silicone can be any organosilicone which yields the desired properties although polydimethylsiloxane (PDMS) is often chosen.

The adhesive layer may be applied directly to the outer contact surface of the flange element to a desired thickness or in combination with one or more primer layer and or one or more primer layers in combination with one or more adhesion or binding promotor layers to create a lamination stack of materials to a desired thickness. As used herein a "primer" is a substance used as a preparatory coating, acting as a joining surface between the contact surface of the negative pressure therapy device and adhesive layer or an adhesion promoting layer and the adhesive layer. Further, an adhesion promoting layer is a substance used as a coating to preferentially adhere the adhesive layer to the contact surface of the negative pressure therapy device and or the primer layer that is applied to the outer surface of the negative pressure therapy device.

By way of example, a primer layer may be applied to the contact surface of the negative pressure therapy device to a thickness of about 0.005 inches, followed by an adhesive promoting layer to a thickness of approximately 0.005 inches, followed by the application of an adhesive layer to a thickness of approximately 0.040 inches achieving a final thickness of approximately 0.050 inches. A primer layer may be applied directly to the outer contact surface of the negative pressure therapy device followed by the application of the adhesive layer directly to the primer to a desired thickness of approximately 0.050 inches. In additional embodiments, an adhesive promoter may be applied to the contact surface of the negative pressure therapy device followed by the application of the adhesive layer to a desired thickness of approximately 0.050 inches.

In certain embodiments the adhesive layer is a gel layer. As used herein a gel layer is a layer of material that can have properties that are mostly liquid however behave like solids due to the cross-linked nature of its structure. The material chosen for the gel layer may be of a certain cohesive pliable consistency so as to mold to and conform to complex shapes for example imperfections in the skin. As used herein cohesive pliable consistency, elasticity or firmness of the gel layer is defined as the gel layer's ability to flow, mold and stretch and substantially return its original shape when not applied to a surface. The material chosen for the gel layer may also be of a certain tack so as to mechanically secure to the contact area. As used herein tack is defined as the gel's "stickiness" and is the property that allows the immediate formation of a bond on contact with another surface The adhesive layer material must adhere sufficiently to the therapeutic device such that it stays adhered to the device when the device is removed from the user's skin. Additionally, must have a tack level that is chosen for appropriate performance at the user's skin interface. That is, at too great a level of tack removal of the device from the skin can be difficult, painful or injurious. While insufficient tack can allow the device to move during use or allow the seal to the skin to open thereby losing the vacuum. The level of tack can be measured by a texture analyzer. For example, using a TA.XT plus with a 7 mm radius and 1 inch diameter spherical head the peak adhesion values should be in a range of 200 to 400 grams peak force more preferably 250 to 350 grams peak force and most preferably 275-325 grams peak force.

As discussed above the tack of the adhesive layer is optimized to achieve a releasable but mechanical anchor of the therapy device to the patient. In certain embodiments the contact surface of the flange element is coated with a primer to preferentially anchor the adhesive layer to the negative pressure therapy device over the contact region of the user.

In certain embodiments the adhesive layer is formed from a washable silicone gel such that when washed and allowed to dry, the adhesive layer returns towards an initial tack. In certain embodiments the silicone gel is chosen from a group with properties that can be controlled including, but not limited to: cross sectional thickness, degree of crosslinking (and thereby firmness and tack) and viscosity (so as to be processable under desired conditions. As used herein viscosity is measured in cps referring to centipoise (cps) were 1 cps=0.01 g/cm/s.

In an embodiment of the invention the gel layer is a prepared from a two-part platinum cured organosilicone mixture with properties equivalent to a silicone gel base having an uncatalyzed viscosity of about 20,000 cps and a crosslinker having an uncatalyzed viscosity of about 300 cps. The final firmness (cps) of the cured gel may be increased by increasing the proportion of the crosslinker in the mixture or decreased by lowering the proportion of the crosslinker in the mix. The tack of the material can be increased by decreasing the proportion of crosslinker in the mixture or decreased by increasing the proportion of crosslinker in the mix. In order to achieve the desired properties using a silicone gel base of 20,000 cps and a crosslinker of 300 cps, the ratio of silicone gel base to crosslinker may range (in parts by weight) from about 10.0:0.01 to about 10.00:10.20

In embodiments of the invention the ratio of 20,000 cps silicone gel base to 300 cps cross linker may further range from about 10.0:0.01 to about 10.0:0.5. In other embodiments of the invention the ratio of 20,000 cps silicone gel base to 300 cps crosslinker may range from about 10.0:0.01 to about 10:0.1. And in further embodiments of the invention the ratio of 20,000 cps silicone gel base to 300 cps crosslinker may range from about 10.0:0.06 to about 10:0.20

By example of the invention the silicone gel base and the crosslinker are mixed in desired ratios and placed under vacuum in order to remove any bubbles in the mixed solution (de-gassing). Following de-gassing, the silicone gel solution is applied to the contact surface of the flange element and allowed to cure. The mixture can achieve full cure in approximately 24 hours at room temperature however in some embodiments a full cure of the silicone gel may be achieved in about 5 minutes by placing the therapy device containing the silicone gel layer at about 150° C. The cure temperature may be adjusted to suit limiting elements of the therapy device, for example lower melting points of other therapy device elements.

In certain embodiments the adhesive layer is made of a hydrogel. Hydrogels are a three dimensional network of crosslinked hydrophilic polymer chains that can be crosslinked either physically or chemically. Due to the hydrogel materials significant water content, hydrogels can resemble natural soft tissue more than any other type of polymeric biomaterial. In further embodiments the hydrogel layer may be found as a hydrocolloid wherein the colloid particles are hydrophilic polymers dispersed in water.

In certain embodiments the adhesive layer is made of a combination of materials applied side-by side on the outer contact surface of the fluidly sealed chamber element. By way of example, a hydrogel material may be applied to the circumference of the center portion of the outer contact surface of the fluidly sealed chamber element and a silicone gel material may be applied on either side peripheral to the hydrogel material. In further embodiments where a combination of materials are applied side-by-side on the outer contact surface of the flange element, a silicone gel layer may be applied to the circumference of the center portion of the out contact surface of the fluidly sealed chamber element and a hydrogel material may be applied to either side peripheral to the silicone gel material followed by a final application of a silicone gel material peripheral to the hydrogel material.

As used herein, "user compliance" refers to the patient's adherence to the prescribed usage of a therapy device for example the usage of a device throughout a sleep cycle.

As used herein, "device compliance" refers to the ability of the device or elements of the device to accommodate variation, for example, bending, twisting, compressing and or expanding of the device in response to device application and usage including anatomical variations of the patient.

Aspects of the device may be made of a generally rigid material. The term "generally rigid" as used herein refers to a material which is sufficiently rigid to maintain the integrity of the particular element in question. The skilled artisan will understand that a number of polymers may be used including thermoplastics, some thermosets, and elastomers. Thermoplastic materials become flowing liquids when heated and solids when cooled, they are often capable of undergoing multiple heating/cooling cycles without losing mechanical properties. Thermoset materials are made of prepolymers which upon reaction cure irreversibly into a solid polymer network. Elastomers are viscoelastic materials which exhibit both elastic and viscous properties and can be either a thermoplastic or thermoset. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

Aspects of the device may be formed using a number of methods known to those of skill in the art, including but not limited to injection molding, machining, etching, 3D printing, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold-in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The therapy device of the present invention comprises structural member(s) that interfaces outside a targeted therapy area of a patient. In a preferred embodiment the therapy area is that of the upper airway. The therapy device contains a chamber element 100 that is used to create a vacuum between an inner surface of the appliance and the skin of the upper neck/chin region. The chamber element 100 is secured to a flange element 105 at a single point along the back of the flange element that evenly distributes the force across all of the flange element. The chamber element 100 may contain one or more compressible recesses 135 and 155 to further assist in evenly distributing force across all of the flange element 105. The chamber element 100 may also have an aperture 115 for the insertion of a vacuum source and an O-ring like feature 110 around the inner circumference of the aperture to assist in the sealing of the vacuum source to the chamber element 100. The device may be formed, molded, or fabricated from any suitable material or combination of materials. Non-limiting examples of such materials suitable for constructing the therapy appliance include plastics, metals, natural fabrics, synthetic fabrics, and the like. The device may also be constructed from a material having resilient memory such as, but not limited to, silicone, rubber, or urethane.

Figure 5:
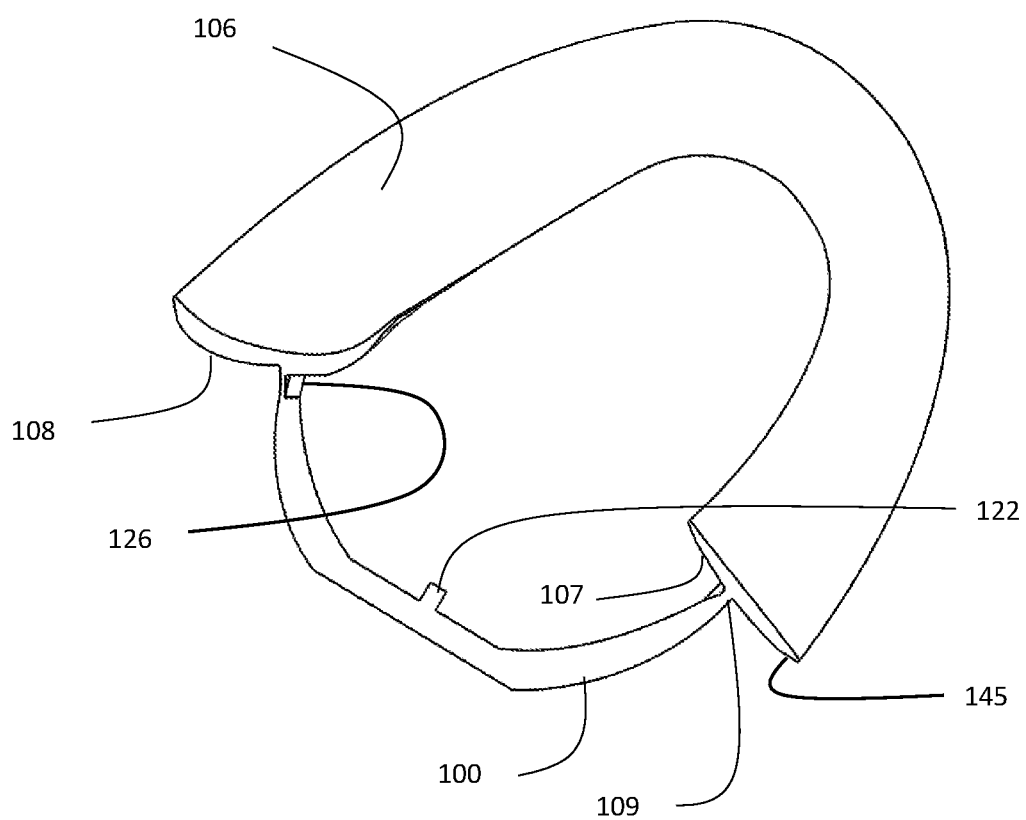
FIG. 5 is a cross-sectional side view (FIG. 4, 140) of an illustrative embodiment the therapy device, showing the chamber element 100, contact surface of the flange element 106, flange element to chamber element junction/root 109, air pump orientation tab 122, a cross section of the chin/mandible recess 125 and tapered edge(s) of the flange element 145.

In an embodiment of the invention, as can be seen in FIG. 5. showing a cross-sectional view 140 of the negative pressure therapy device, the device contains a chamber element 100 in the form of a dome, the chamber element having a mandible recess(s) 135 and a flange element 105 with an outer contact surface of the flange element 106 configured to conform to approximately the upper airway of a user, the flange element containing tapered edges 145 to ensure a smooth transition on the skin of the user and eliminate edge effects.

Figure 6A:
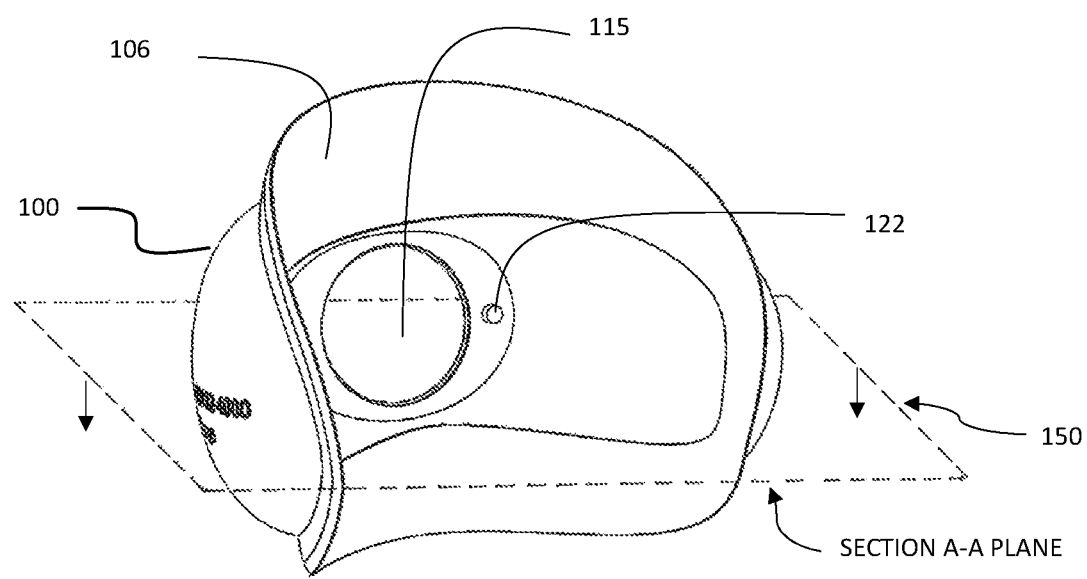
FIG. 6a is a rear view of an illustrative embodiment of the invention showing the therapy device chamber element 100, contact surface of the flange element 106, inside root flange element width 107, air pump aperture 115, air pump orientation tab 122 and a section plane 150 along A-A for purposes of FIG. 6b.
Figure 6B:
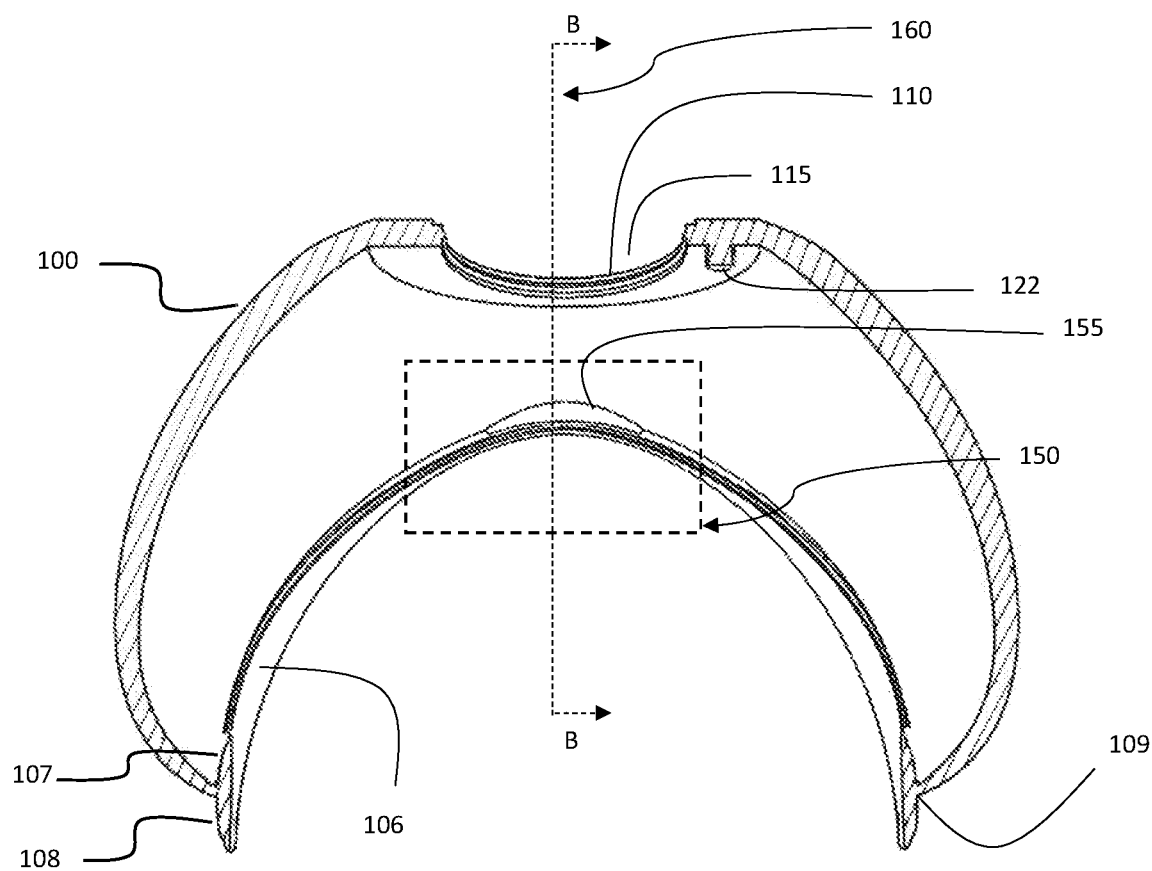
FIG. 6b is a sectional view along plane A-A showing the bottom of the therapy device with the chamber element 100, contact surface of the flange element 106, flange element to chamber element junction/root 109, O-ring feature 110, air pump aperture 115, air pump orientation tab 122, neck relief recess 155, neck relief detail box 150 for FIG. 6c and a section plane 160 along B-B for purposes of FIG. 6d.
Figure 6C:
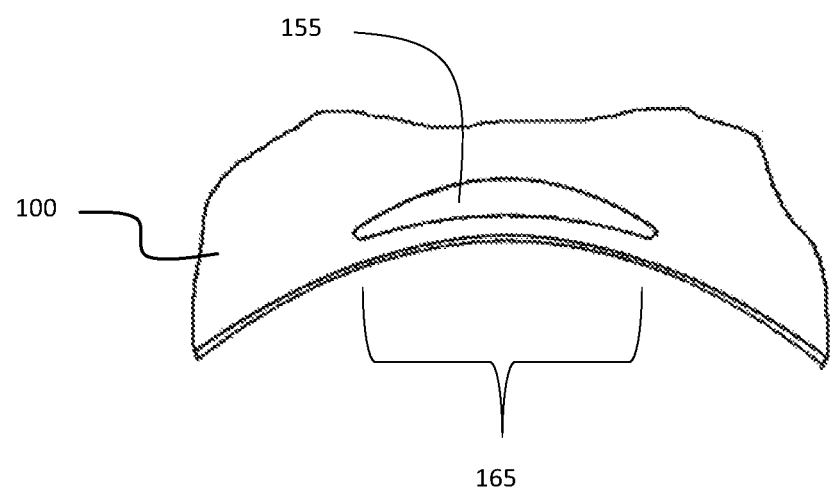
FIG. 6c is a detail view 150 of the neck relief recess 155, showing a portion of the chamber element 100 and the compressible region that approximately conforms with location four on the user at approximately the laryngeal prominence 165.
Figure 6D:
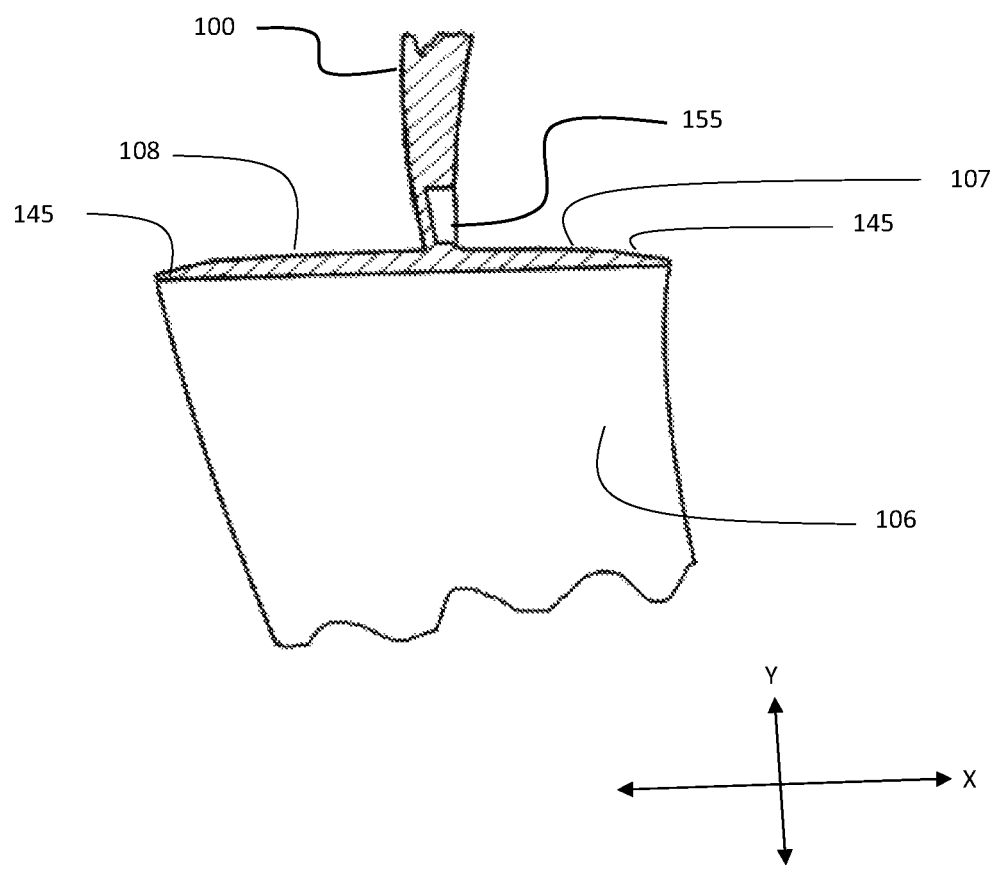
FIG. 6d is a section view along plane B-B 160, showing a section of the chamber element 100, contact surface of the flange element 106, inside root flange element width 107, outside root flange element width 108, tapered edge(s) of the flange element 145 and neck relief recess 155.

FIG. 6*a*-6*d* show cross-sectional views the device. FIG. 6*b* shows a cross-sectional view of the device across the A-A plane FIG. 6a including the chamber element 100, the contact surface of the flange element 106, the compressible neck recess 155, the air pump aperture 115 and O-ring feature. FIG. 6c shows a detailed view, FIG. 6b 150, of the compressible neck recess 155 in a crescent shape following the contour of the edge of the chamber element and the region of compression 165 that extents from one corner of the crescent to the other. FIG. 6d shows a cross-sectional view of the chamber element 100 with the contact surface of the flange element 106, a cross-sectional side view of the compressible neck recess 155 and tapered edges of the flange element 145.

Figure 7:
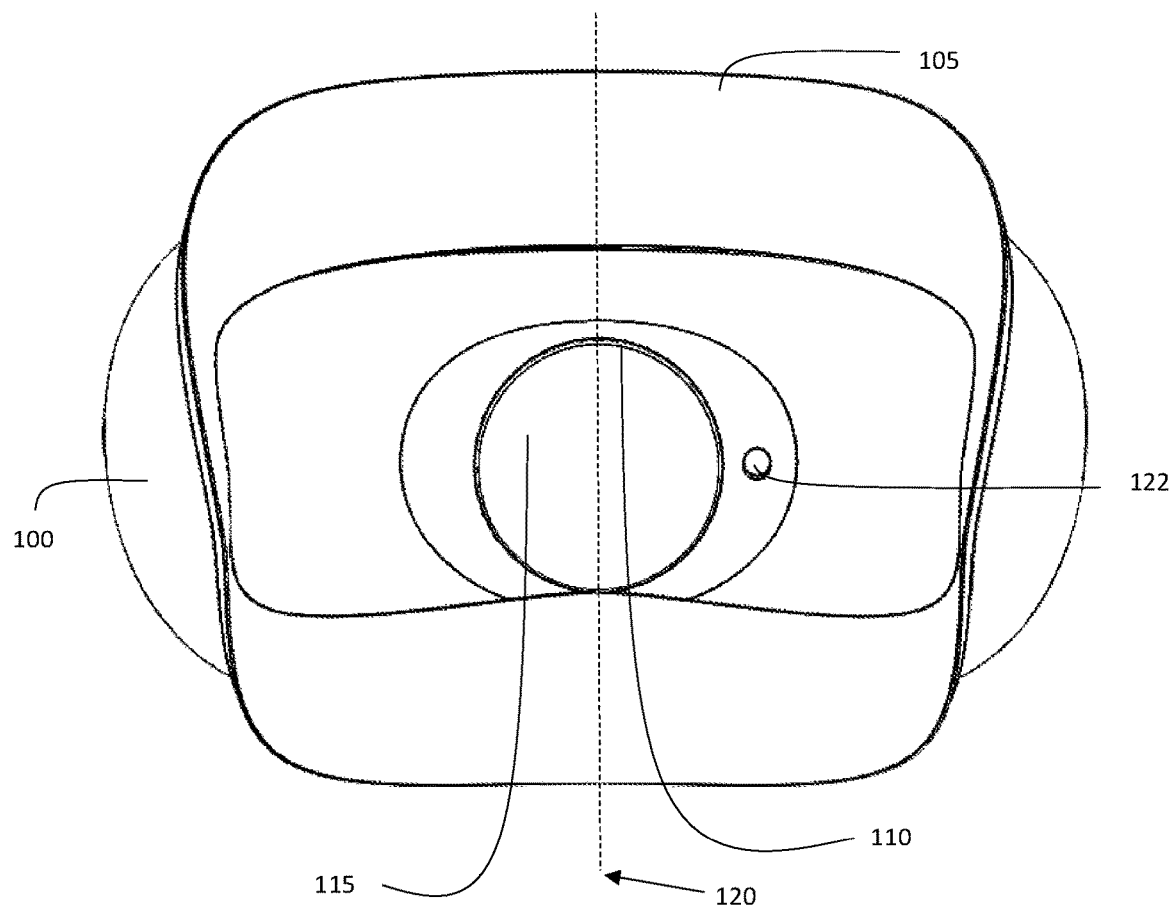
FIG. 7 is a three dimensional rear view of an illustrative embodiment of the therapy device including the chamber element 100, the contact surface of the flange element 106, the O-ring feature 110, air pump aperture 115, and vertical line bisecting the therapy device 120 for purposes of FIG. 8.
Figure 8:
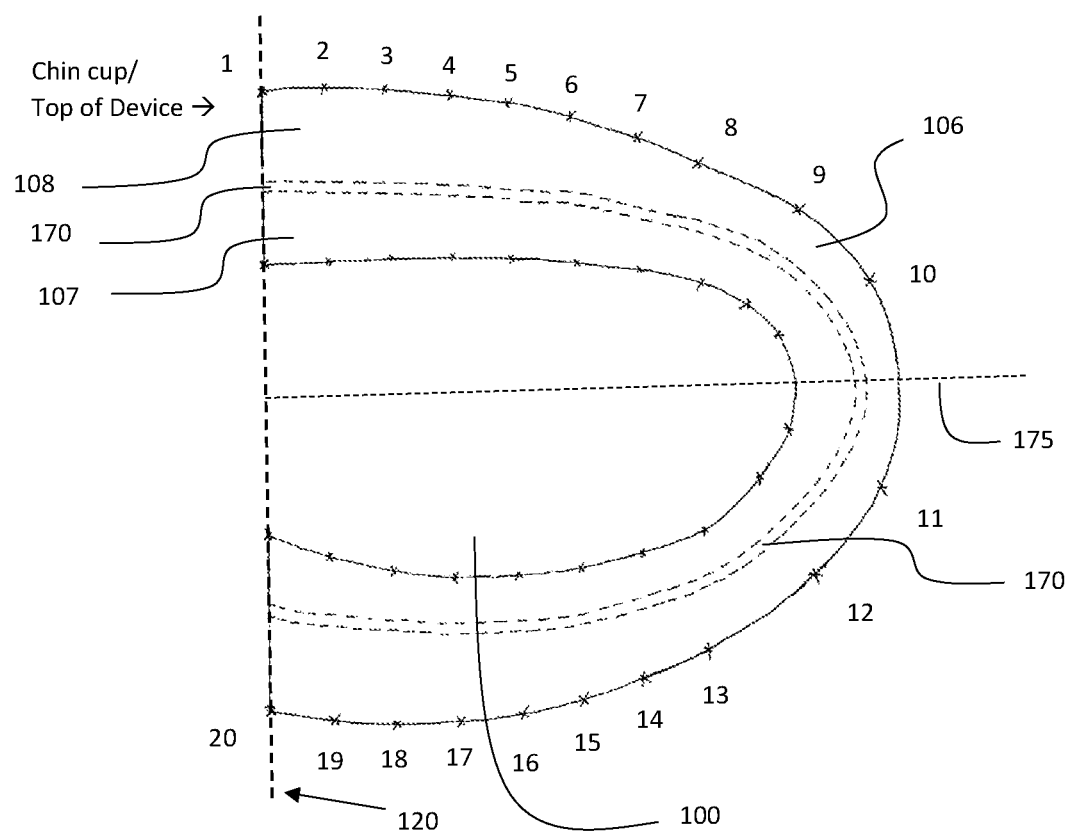
FIG. 8 is a two dimensional rear view of an approximate trace of half the therapy device, where the therapy device is pressed against a flat surface and traced along its edges. The trace is bisected along the vertical axis 120 of the therapy device (FIG. 7, 120), showing the flattened half of the chamber element 100 including the flattened contact surface of the flange element 106, the inside root flange element width 107, the outside root flange element width 108, the flange element further having parallel dashed lines 170 showing the root/junction 109 of the chamber element on the flange element, approximately following the curvature of the flange element as an approximate example of the location(s) of the chamber element of the surface distal to contact surface of the flange element, the contact surface of the flange element divided into stations 1-20 for graphical representation in FIG. 9-FIG. 14.

The flange element 105 is designed to accommodate variations in station load upon placement of the therapy device on a subject and application of a therapeutic level of negative pressure. This is accomplished by device design and structural elements that anticipate known anatomical features as well as structural elements that can accommodate surface variations that occur during use. FIG. 7, showing the rear of the therapy device with the chamber element feature 100 and contact surface of the flange element 106 has a line bisecting the device 120 for purposes of FIG. 8. In order to further graphically illustrate the cushioning feature(s) of the device, FIG. 8 shows a flattened/two-dimensional approximate tracing of half of the therapy device with chamber element 100 and contact surface of the flange element 106, with the bisecting line 120 as seen in FIG. 7 and parallel dashed lines 170 following the flange element 106 showing the approximate junction/root 109 of the chamber element 100 on the rear of the flange element (distal to the contact surface of the flange element). The location of the root 109 can vary on the flange element to increase or decrease the vacuum cross section. A larger inside root length 107 as compared to the outside root length 108 will effectively increase the vacuum cross section and conversely a larger outside root length as compared to inside root length will effectively decrease the vacuum cross section.

The flattened half of the contact surface of the flange element 106 is approximately sectioned into 20 stations beginning at station 1, located closest to the upper middle section of the device at location two on the user, that makes contact approximately with the chin of the user, progressing through stations 8-13 traveling over approximately the first and third locations on the user, over approximately the mandible and gonion approaching the ear and down to the neck toward station 20 located at the bottom portion of the half of the flange element located approximately at location four on the user at approximately at the middle of the neck of the user. Located approximately and/or approximately positioned, as used herein describes a location closer to one point verses another but perhaps not exactly at one exact positon or another for example: "located approximately at location four on the user at approximately the middle of the neck of the user" describes the location being nearer to the middle of the neck of the user than location(s) one and three corresponding to the mandible and gonion of the user.

Figure 10:
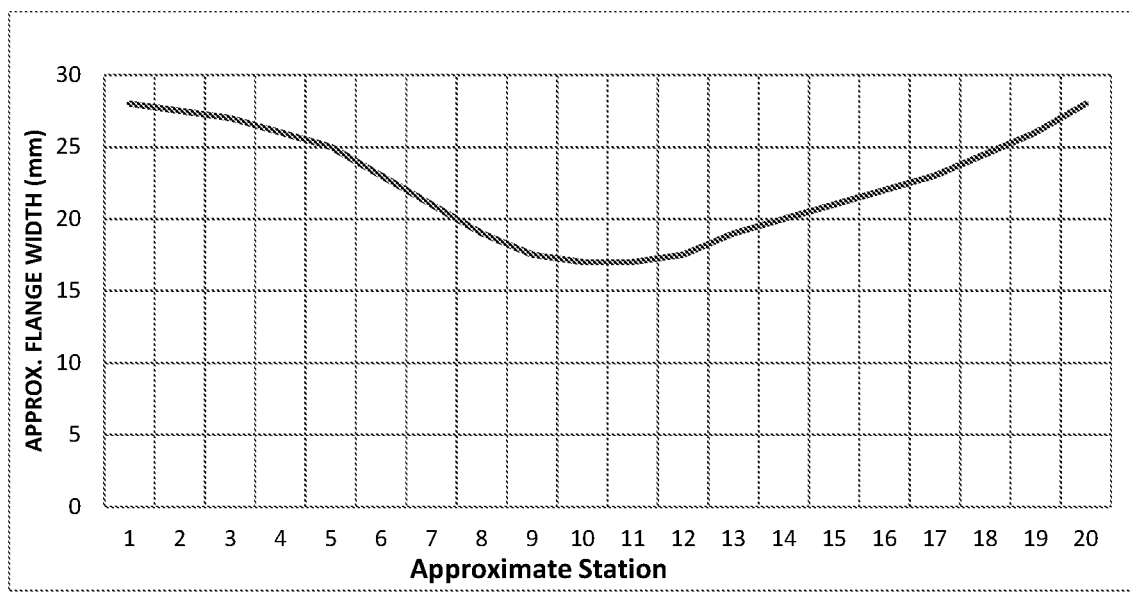
FIG. 10 is a graphical representation of the approximate flange element width along stations 1-20.
Figure 11:
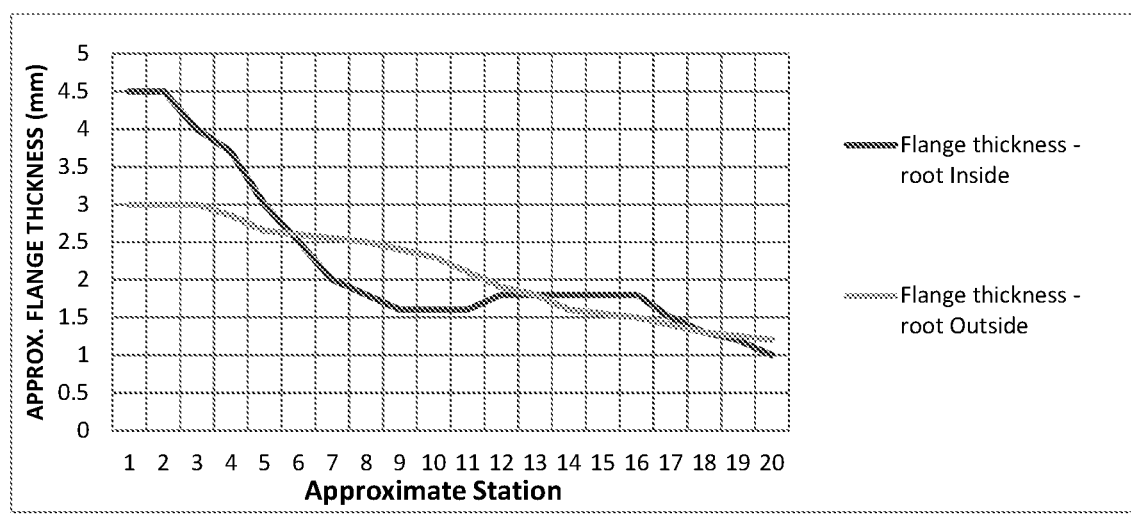
FIG. 11 is a graphical representation of the approximate flange element thickness on the outside of the root and approximate flange element thickness inside the root.

Absent features, for example a specific chamber element orientation on the flange element FIG. 8, 170 or the compressible recesses 135 and 155 or a flange element of varying widths FIG. 9 and FIG. 10 or thicknesses FIG. 9 and FIG. 11 (and structural features therein) to balance the contact pressure of the device when a therapeutic level of negative pressure is applied, a user would experience varied contact pressures, for example, lower contact pressure in regions where the cross section of the dome decreases due to the non-symmetric shape of the dome for example at the tips of the oval shaped dome/at the ends of the device, specifically through approximately stations 8-13 FIG. 8, or higher contact pressure in regions where there is a large vacuum cross section, for example through approximately stations 1-3 and 18-20. Therefore these areas contain cantilever and hoop structure-type features FIG. 12, that alone or together equalize the contact pressure through the entire contact surface of the flange element giving a station load on the user of a non-varying or minimally varying value, FIG. 13.

The characteristics of the flange element and chamber element are adjusted to accommodate for the variation in anatomy that necessitate the shape of the device, for example where the device encounters bends around at approximately location two on the used at approximately the chin/mandible, at approximately stations 2-4 and at approximately location four at approximately the lower neck, at approximately stations 17-20 the flange element predominantly experiences hoop-forces that, absent design features would stiffen the flange element creating a high point load. Therefore, hoop-forces that cause stiffening of the flange are balanced in part by varying the perpendicular width (FIG. 9, FIG. 10 and FIG. 14, 185) and thickness (FIG. 9 and FIG. 11)of the flange element, for example in FIG. 10, stations 1-4 and 17-20 are wider and thinner allowing for more flexibility.

Figure 12:
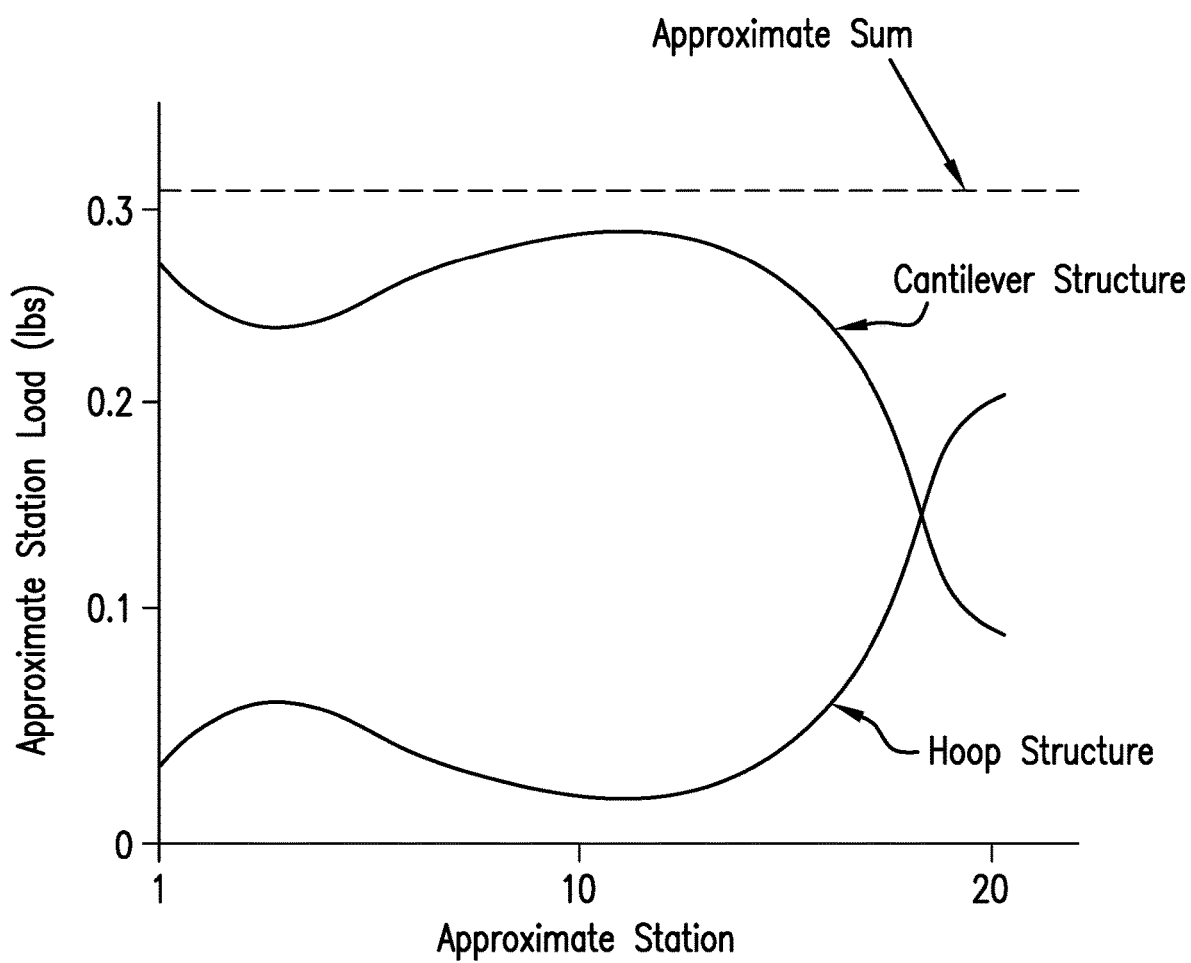
FIG. 12 is a graphical representation of the approximate balancing loads provided by cantilever structure elements and hoop structure elements of the therapy device along stations 1-20 for the purpose of balancing station loads.
Figure 13:
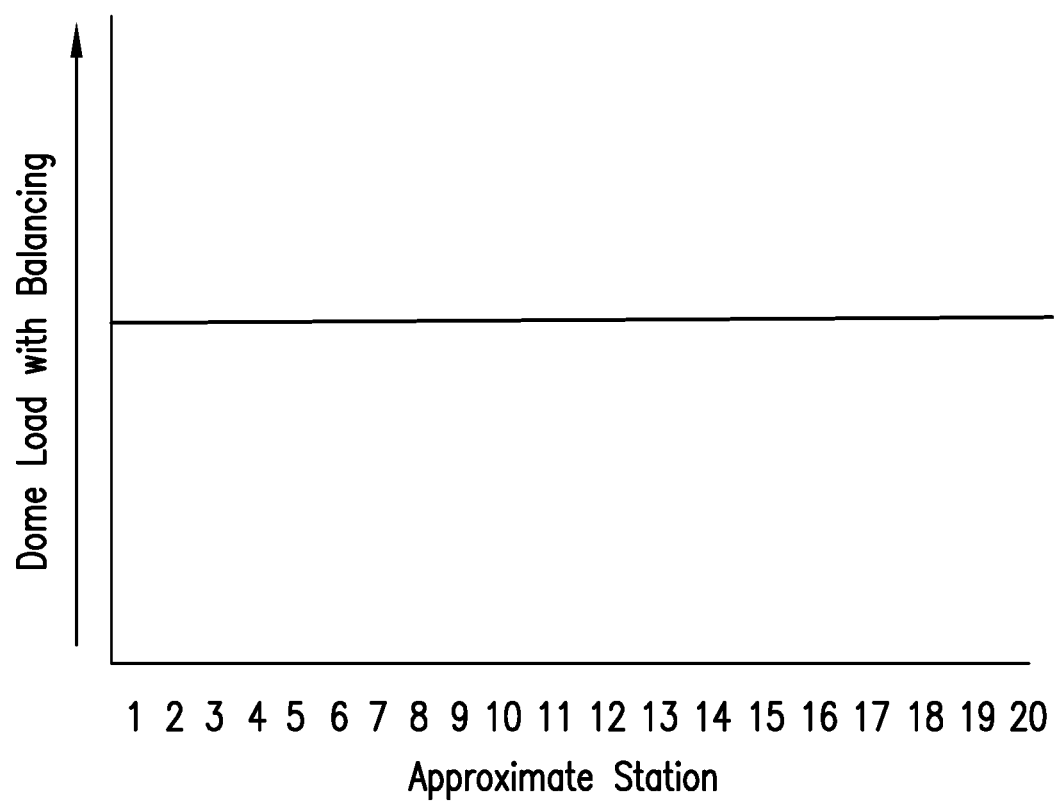
FIG. 13 is a graphical representation of the approximate station load variation along stations 1-20 when accommodating structural features are incorporated into the device, the device is placed on the user and a therapeutic level of negative pressure is applied.

In areas where the flange element lays flatter on the user, for example at approximately stations 5-15 the flange element predominantly experiences cantilever forces, FIG. 12, therefore cantilever structures are present to capture and balance the contact pressure. For example, at approximately stations 5-15 the width of the flange element decreases FIG. 9 and FIG. 10. The combination of the balancing features of the therapy device provide for an approximate balancing of the observed contact pressure FIG. 14, 200, of the therapy device on the user when a therapeutic level of negative pressure is applied. For example, FIG. 13 shows the approximate station load variation when all structural features are combined and a therapeutic level of negative pressure is applied.

Figure 14:
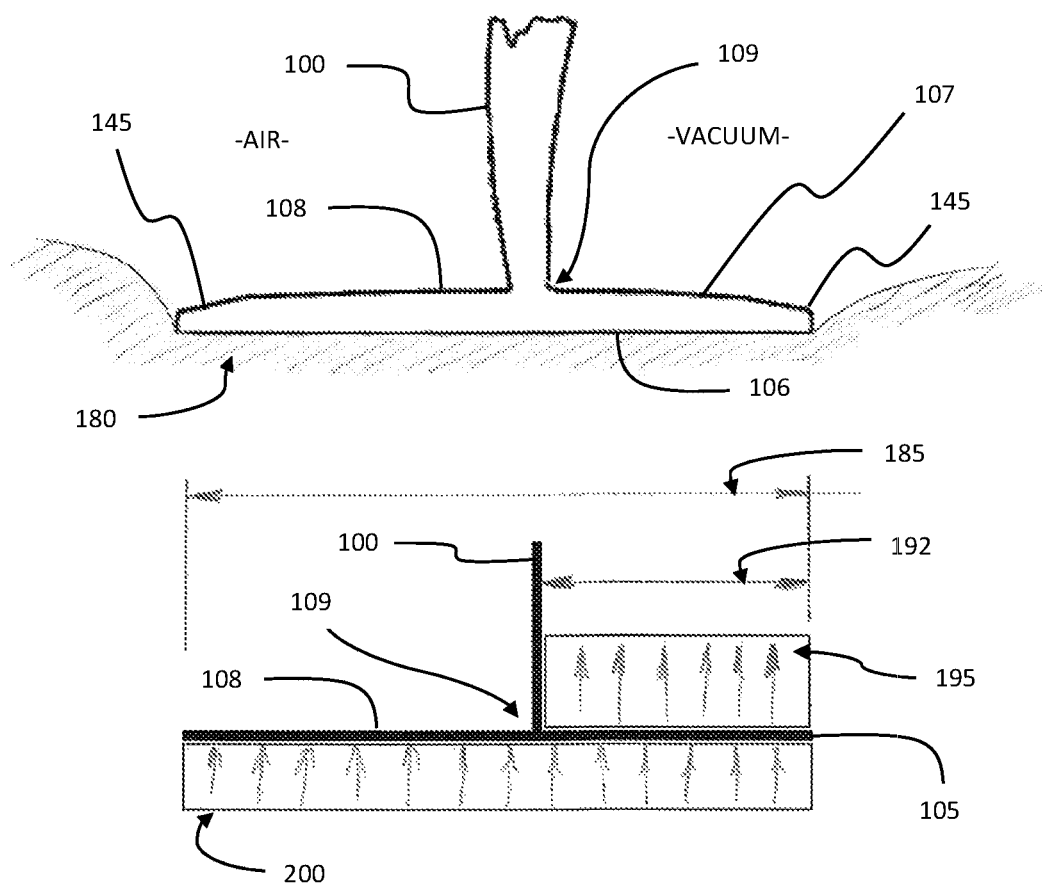
FIG. 14 is a cross sectional view 160 of an illustrative embodiment of the therapy device showing the vacuum side (root inside) 107 and air side (root outside) 108 of the device, the chamber element 100, flange element 105, contact surface of the flange element 106, tapered edge(s) of the flange element 145, a representation of compressed tissue 180, the root/junction/balance point 109 of the chamber element 100 on the flange element 105, total flange element width (perpendicular width) 185, chamber element bias on the flange element 192 (root inside) 107, acting vacuum portion of the flange element 195 and contact pressure representation of the flange element on the user 200.

Further illustration of the therapy device can be seen in FIG. 14 that shows a cross section 160 of the therapy device, with the chamber element 100, flange element 105, contact surface of the flange element 106, vacuum side (root inside) 107 and air side (root outside) 108 of the device, the root/junction/balance point 109 of the chamber element on the flange element, total flange element width (perpendicular width) 185, chamber element bias on the flange element 192 (root inside) 107, acting vacuum portion of the flange element 195 and contact pressure representation of the flange element on the user 200.

In certain embodiments the perpendicular width FIG. 14, 185 of the flange element is varied to increase or decrease the contact pressure 200 at certain stations along the contact surface of the flange element 106. A decrease in the perpendicular width 185 reduces the station area ultimately increasing the contact pressure for that segment area when a therapeutic level of negative pressure is applied. For example, in FIG. 8 as one approaches stations 8-13 one can see the perpendicular 185 width decreases. Therefore, when one combines a known variation in dome station load with a design feature configured to accommodate the variation a lowest possible station pressure variation can be achieved.

Figure 16:
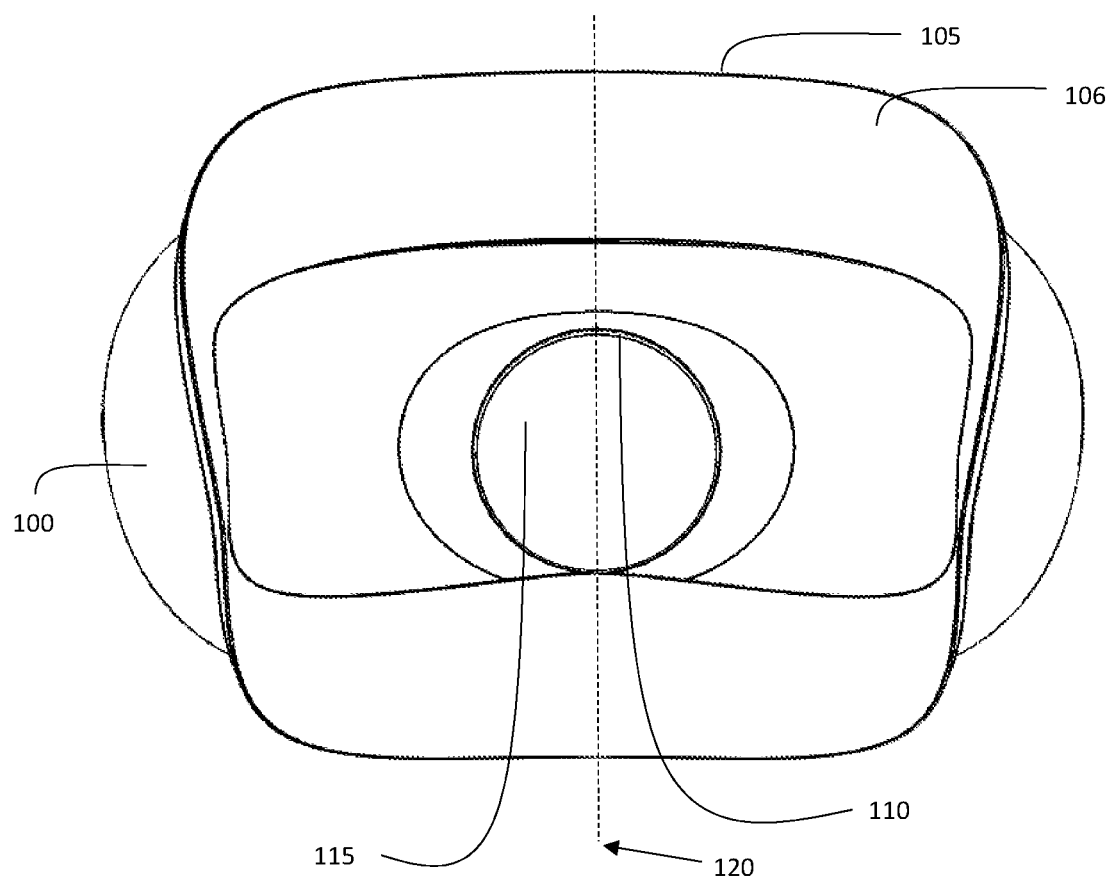
FIG. 16 depicts the rear (the aspect facing the wearer) of the therapy device. A line bisecting the device is shown for purposes of FIG. 17.
Figure 17:
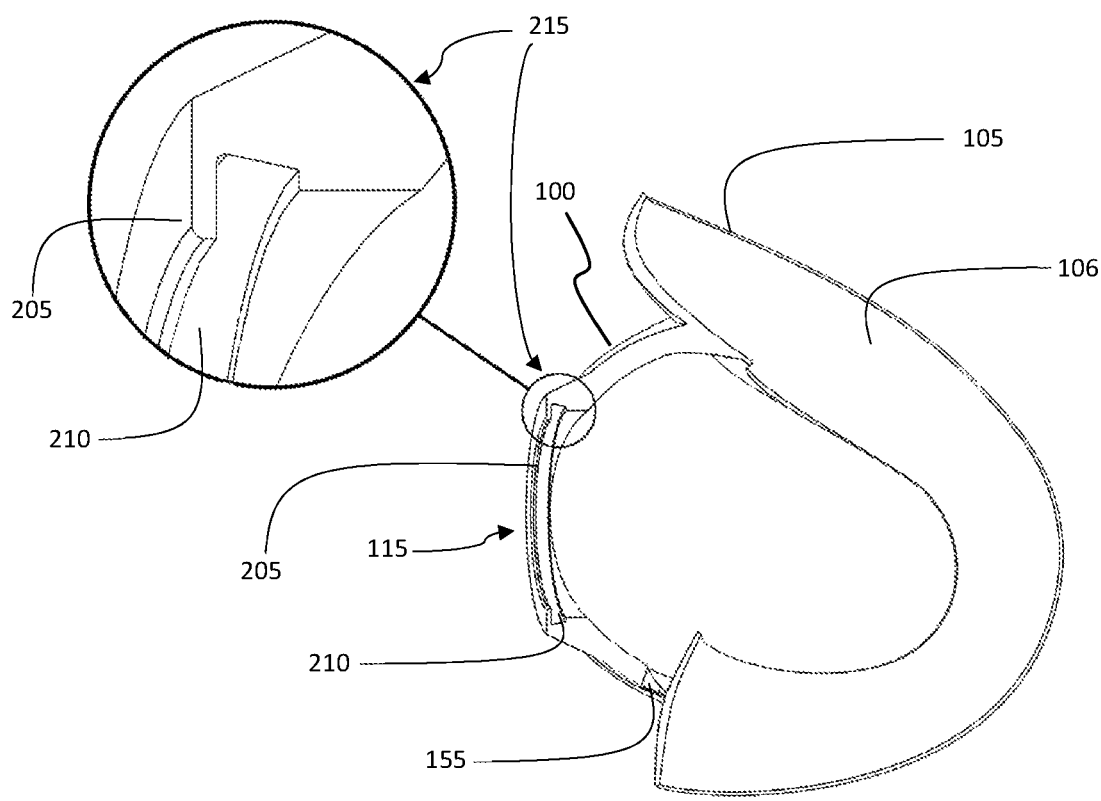
FIG. 17 depicts a three-dimensional view and a detail box of the therapy device of FIG. 16 bisected along the line shown in FIG. 16.
Figure 18:
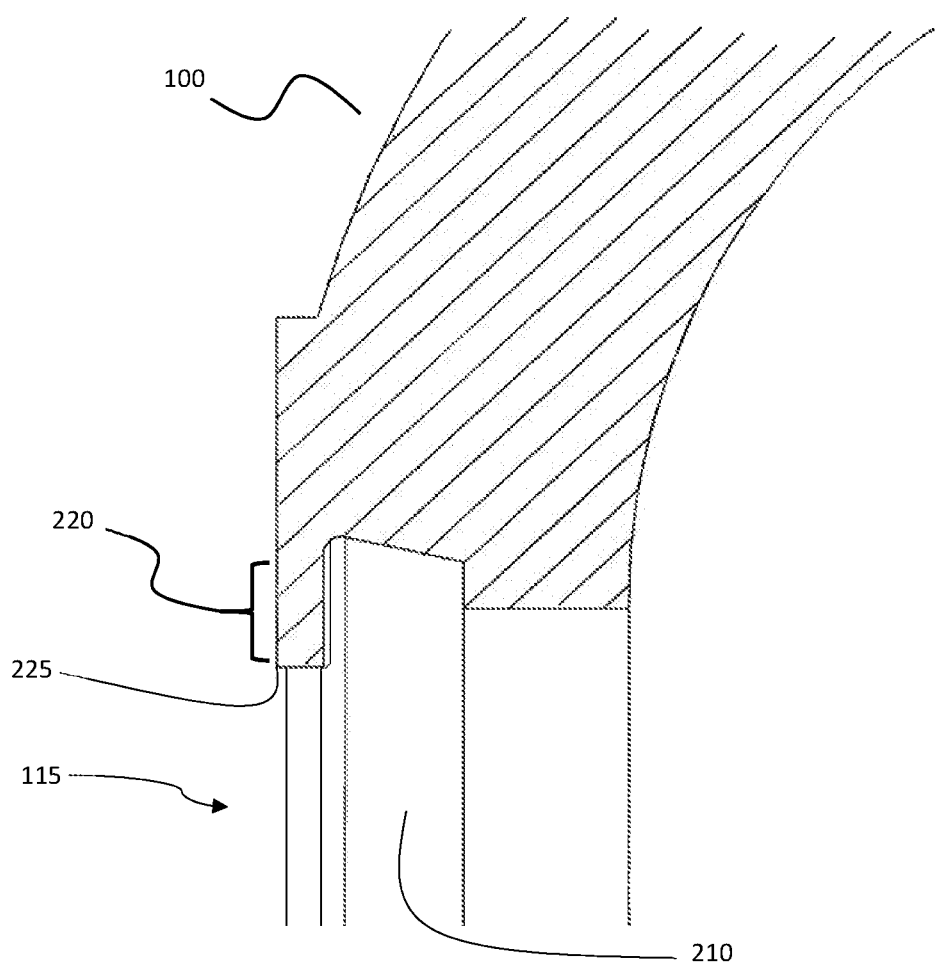
FIG. 18 depicts a detail of a lip-seal feature and lip-seal cavity in a chamber element of the invention.
Figure 19:
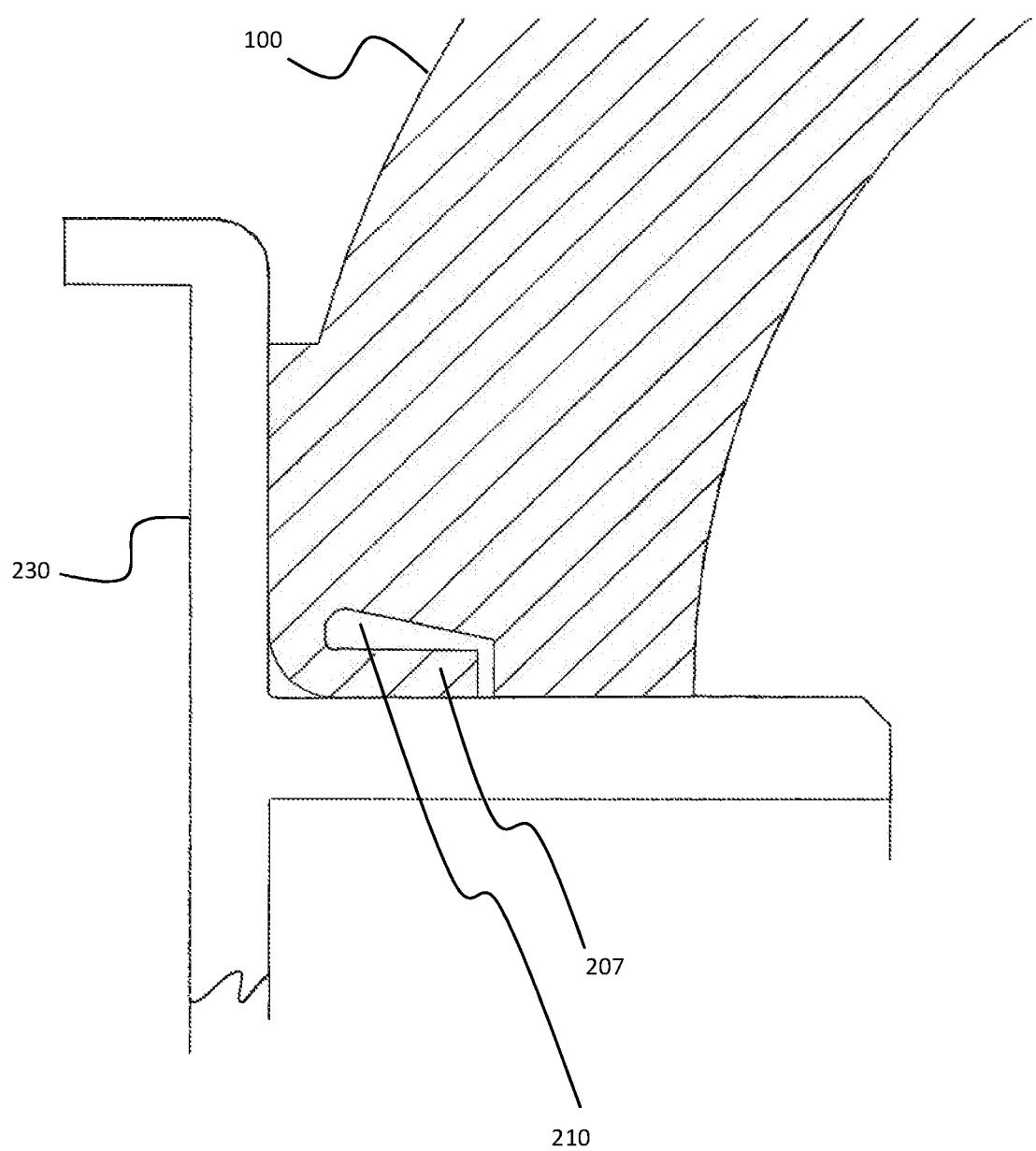
FIG. 19 depicts the lip seal of FIG. 18 upon insertion of a pump housing element.

The compliant sealing ring 110 is designed to create and maintain an air tight seal between the chamber element 100 and the pump hosing element FIG. 18; 230. In certain embodiments, the sealing ring is in the form of a lip seal 205; FIG. 17, FIG. 18 and FIG. 19. FIG. 16, showing the rear of the therapy device with the chamber element 100, the flange element 105, contact surface of the flange element 106 element has a line bisecting the device 120 for purposes of FIG. 17. In order to fully illustrate the lip-seal feature 205 of the device, FIG. 17 shows a three-dimensional view and a detail box 215 of the chamber element 100 with a pump aperture 115 containing a lip-seal 205 and lip-seal cavity 210 to receive the lip-seal during use, also seen in this view is the compressible recess 155 located on the chamber element a position approximately corresponding to the laryngeal prominence, FIG. 15A.

The lip-seal feature 205 and lip-seal cavity 210 of the chamber element 100 can be seen in FIG. 18 wherein the lip-seal 205 is uncompressed and in an un-biased positon without the pump housing element installed. The surface of the lip-seal that will make contact with the pump housing element begins with the lip-seal edge 225 and continues along the lip-sealing surface 220. Upon insertion of the pump housing element 230; FIG. 19, the lip-seal 205 is folded in approximately 90 degrees into the lip-seal cavity 210 and is in is deflected position 207.

Device balancing may also be accomplished through variation in other structural elements of the chamber element or flange element both locally and throughout the contact surface, for example length or width of compressible recesses, chamber element or flange element thickness and shape of the central bend of the device alone, whole or in part. In a preferred embodiment the structural elements including the aspect ratio of the flange element may change to provide minimal variation in contact pressure wherein the contact pressure is approximately 1.2 times that of the applied vacuum at all contact points of the flange element.

Structural embodiments of the apparatus may vary based on the size of the device and the description provided herein is a guide to the functional aspects and means.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims:

1. A therapy device configured for the administration of negative pressure upon an external surface of an individual, the therapy device comprising:
   a chamber comprising
   (i) a flange element defining a periphery of a chamber element and adapted to form a sealing surface when mated to the individual, wherein a first surface of the flange element is configured to approximately conform to a continuous contact area on the individual defined by a first location corresponding to a first gonion on one side of the individual's mandibular body, a second location corresponding to the individual's mental protuberance, a third location corresponding to a second gonion on the opposite side of the individual's mandibular body, and a fourth location corresponding to the individual's thyroid cartilage,
   (ii) the chamber element affixed to the flange element such that an airtight junction is provided between the flange element and the chamber element, wherein the chamber element is configured to define a chamber overlying the external surface of the individual bounded by the flange element and to apply a force to the external surface of the individual when a therapeutic level of negative pressure is applied within the chamber element, the force sufficient to maintain patency of the upper airway of the individual by drawing the external surface of the individual into the chamber element,
   (iii) one or more first recesses in the form of a localized thinning in a material forming the chamber element, located in an internal surface of the chamber element approximately at a junction formed between the flange element and the chamber element at the second location, the first recesses providing a first hinge region within the chamber element, and
   (iv) one or more second recesses within the chamber element in the form of a localized thinning in the material forming the chamber element, located in the internal surface of the chamber element approximately at a junction formed between the flange element and the chamber element at the fourth location, the second recesses providing a second hinge region within the chamber element,
   wherein the first and second hinge regions are configured (i) to reduce the transmission of deformational strain within the chamber element and (ii) to reduce point loads where the flange element contacts each of the individual's mental tubercles and the individual's thyroid cartilage when the therapeutic level of negative pressure is applied within the chamber element, the reductions in the transmission of deformational strain and in the point loads being relative to a chamber element lacking the first and second hinge regions;
   wherein the flange element varies in thickness such that the first and third locations are substantially thicker than the fourth location;
   wherein the junction formed between the flange element and the chamber element at the first and third locations are positioned on the flange element such that at least 20% of the width of the flange element is positioned within the interior of the chamber element; and an air pump operably connected to the chamber element to produce the therapeutic level of negative pressure within the chamber element.

2. The therapy device of claim 1, wherein the chamber element comprises two first recesses approximately positioned at the individual's mental tubercles.

3. The therapy device of claim 2, wherein a location on the width of the flange element at which the junction is formed between the flange element and the chamber element varies around the circumferential dimension of the flange element such that, when a therapeutic level of negative pressure is applied within the chamber element, the force applied to the external surface of the individual at any point along the circumferential dimension of the flange element is within 20% of the average force along the entire circumferential dimension of the flange element, wherein the force at each point along the circumferential dimension of the flange element is measured at the location on the width dimension of the flange element at the junction formed between the flange element and the chamber element.

4. The therapy device of claim 3, wherein the junction formed between the flange element and the chamber element at the second and fourth locations are positioned on the flange element such that between 30% and 50% of the width of the flange element is positioned within the interior of the chamber element.

5. The therapy device of claim 4, wherein the chamber element is affixed to the flange element as an integral structure.

6. The therapy device of claim 4, wherein the chamber element is affixed to the flange element as a unitary structure.

7. The therapy device of claim 4, wherein the chamber element is affixed to the flange element as discrete structures.

8. The therapy device of claim 1, wherein the one or more first recesses are within the chamber element.

9. The therapy device of claim 1, wherein the one or more second recesses are within the chamber element.

10. The therapy device of claim 1, wherein the flange element comprises a tacky material inherent in, or positioned on, all or a portion of the contact area.

11. The therapy device of claim 10, wherein the tacky material comprises a room-temperature vulcanizing (RTV) silicone.

12. The therapy device of claim 11, wherein the tacky material is a component of a lamination stack of materials positioned on all or a portion of the contact area.

13. The therapy device of claim 1, wherein the flange element is increased in thickness at the junction formed between the flange element and the chamber element relative to the edges thereof.

14. The therapy device of claim 13, wherein, at the first and third locations, the flange element thickness at the junction formed between the flange element and the chamber element is between about 0.05 inches and about 0.120 inches, and the flange element thickness at the edges is between about 0.005 inches and about 0.025 inches.

15. The therapy device of claim 14, wherein, at the second location, the flange element thickness at the junction formed between the flange element and the chamber element is between about 0.05 inches and about 0.20 inches, and the flange element thickness at the edges is between about 0.05 inches and about 0.120 inches.

16. The therapy device of claim 15, wherein, at the fourth location, the flange element thickness at the junction formed between the flange element and the chamber element is between about 0.020 inches and about 0.100 inches, and the flange element thickness at the edges is between about 0.005 inches and about 0.020 inches.

17. The therapy device of claim 16, wherein the flange element has a curved profile on the top surface thereof which provides the increased thickness at the junction formed between the flange element relative to the edges thereof.

18. The therapy device of claim 17, wherein the flange element has a flat profile on the bottom surface thereof.

19. The therapy device of claim 18, wherein the air pump is connected to the chamber element via a hose or tube.

20. The therapy device of claim 18, wherein the air pump is a manual squeeze bulb.

21. The therapy device of claim 18, wherein the air pump is wearable by the patient and is battery powered.

22. The therapy device of claim 18, wherein the air pump is configured integrally to the chamber element.

23. The therapy device of claim 22, wherein the air pump comprises a piezoelectric material configured to provide an oscillatory pumping motion.

24. The therapy device of claim 23, wherein the oscillatory pumping motion operates at a frequency greater than 500 Hz.

25. The therapy device of claim 24, wherein the chamber element comprises an opening into which the air pump engages, wherein when engaged a periphery of the opening forms an airtight seal with the air pump, and wherein the opening comprises a compliant sealing member affixed to the chamber element as a unitary structure into which the air pump engages.

26. The therapy device of claim 25, wherein the compliant sealing ring and the chamber element are discrete structures.

27. The therapy device of claim 1, wherein the chamber element comprises one or more vent elements configured to provide an airflow into the chamber element when the chamber element is mated to the individual and the therapeutic level of negative pressure is applied within the chamber, and wherein the airflow is between about 30 mL/min and about 150 mL/min.

28. A method of performing negative pressure therapy on an individual, comprising:
    mating a therapy device according to claim 1 on the individual to define a chamber element overlying the external surface of the individual bounded by the flange element, wherein the flange element conforms to a continuous contact area on the individual defined by a first location corresponding to a first gonion on one side of the individual's mandibular body, a second location corresponding to the individual's mental protuberance, a third location corresponding to a second gonion on the opposite side of the individual's mandibular body, and a fourth location corresponding to the individual's thyroid cartilage; and
    applying a therapeutic level of negative pressure within the chamber element.

* * * * *